US006943026B1

(12) United States Patent
Balmain et al.

(10) Patent No.: US 6,943,026 B1
(45) Date of Patent: Sep. 13, 2005

(54) ANTITUMOUR VECTOR CONSTRUCTS AND METHODS

(75) Inventors: Allan Balmain, Glasgow (GB); Jing de Zhu, Glasgow (GB)

(73) Assignee: Cyclacel Limited, Scotland (GB)

( * ) Notice: Subject to any disclaimer, the term of this patent is extended or adjusted under 35 U.S.C. 154(b) by 0 days.

(21) Appl. No.: 09/051,159

(22) PCT Filed: Oct. 2, 1996

(86) PCT No.: PCT/GB96/02416

§ 371 (c)(1),
(2), (4) Date: Jan. 13, 1999

(87) PCT Pub. No.: WO97/12970

PCT Pub. Date: Apr. 10, 1997

(30) Foreign Application Priority Data

Oct. 2, 1995 (GB) .............................................. 9520079
Aug. 8, 1996 (GB) .............................................. 9616685

(51) Int. Cl.[7] .............................................. C12N 15/63
(52) U.S. Cl. ..................... 435/455; 435/320.1; 435/325; 435/252.3; 424/93.2; 536/23.2; 536/24.1
(58) Field of Search .............................. 435/455, 320.1, 435/325, 252.3; 424/93.2; 536/23.2, 24.1, 23.1; 514/44

(56) References Cited

U.S. PATENT DOCUMENTS

| | | |
|---|---|---|
| 5,700,657 A | 12/1997 | Beaudry et al. |
| 6,004,941 A * | 12/1999 | Bujard et al. .................. 514/44 |

FOREIGN PATENT DOCUMENTS

| | | |
|---|---|---|
| DE | 195 02 584 A1 | 3/1995 |
| WO | WO 93/15769 | 8/1993 |
| WO | WO 94/23046 | 10/1994 |
| WO | WO 94/29442 | 12/1994 |
| WO | WO95/16771 | 6/1995 |
| WO | WO 95/19367 | 7/1995 |

OTHER PUBLICATIONS

Gura (Science 278:1041–1042, Nov. 7, 1997).*
Viewig (Cancer Invest. 13(2): 193–201 (1995)).*
Le Beau et al (Nature 316(6031):826–828, 1985).*
Deb et al J. Virol. 66(10): 6164–6170, 1992.*
Blau et. al., Gene Therapy– A Novel form of drug delivery; 1995, The New England Journal of Medicine, vol. 333:1204–1207.*
Crystal, Transfer of Genes to Humans: Early Lessons and Obstacles to Success; 1995, Science vol. 270: 404–410.*
Miller et. al., Targeted vectors for gene therapy, 1995;FASEB , vol. 9:190–199.*
Orkin et. al.; Report and Recommedations of the Panel to Assess the NIH Investment in Research on Gene Therapy, 1995, pp. 1–41.*
Deb et al J. Virol. 66(10):6164–6170.*
Viewig (Cancer Invest. 13(2): 193–201 (1995).*
Le Beau et al (Nature 316(6031): 826–828, 1985).*
Yamaguchi et al (Eur. J. Biochem. (1994) 221: 227–237).*
Symonds et al (J. Virol. (1991) 65(10): 5417–5424).*
Ohashi et al (Genomics (1995) 30(2): 406–407).*
Rotter et al (Mol. Cell. Biol. (1984) 4(2):383–385).*
Deuschle, Tetracycline–Reversible Silencing of Eukaryotic Promoters; 1995, Molecular and Cellular Biology; 1907–1914.*
I. Verma et. al., Gene therapy–promises, problems and prospects, 1997, Nature vol. 389:239–242.*
Ross et. al., Gene therapy in the United States: A five–year status report, 1996; human Gene Therapy 7:1781–1790.*
Fick et al., The Extent of heterocellular communication mediated by gap junctions is predictive of bystander tumor cytoxicity in vitro, 1995; Proc. Natl. Acad. Sci. vol. 92: 11071–11075.*
Beck et. al. , TheThymidine Kinase/Ganciclovir–Mediated "Suicide" Effect Is Variable In Different Tumor Cells, 1995; Human Gene Therapy 6: 1525–1530.*
Orkin et. al.; Report and Recommedations of the Panel to Assess the NIH Investment in Research on Gene Therapy, 1995.*
Deuschle, Ulrich et al., (1995) "Tetracycline–Reversible Silencing of Eukaryotic Promoters", Molecular and Cellular Biology, vol. 15, No. 4, p. 1907–1914.
Pavletich, Nikola et al., (1993) "The DNA–Binding Domain of p53 Contains The Four Conserved Regions And The Major Mutation Hot Spots", Genes & Development, pp. 2557–2564.

(Continued)

*Primary Examiner*—Dave Trong Nguyen
*Assistant Examiner*—Richard Schnizer
(74) *Attorney, Agent, or Firm*—Lahive & Cockfield, LLP; Giulio A. DeConti, Jr.; Cynthia L. Kanik

(57) ABSTRACT

Compositions for targeting expression of a gene such as an antitumor gene may contain a first nucleic acid construct in which expression of a first gene is controlled by a first promoter whose function is suppressed in non-tumor cells, and a second nucleic acid construct in which expression of a second gene for down-regulating the first gene in non-tumor cells is controlled by a second promoter that is up-regulated in non-tumor cells. The second promoter may be regulated by means of p53 binding, targeting expression of the first gene to cells in which p53 down-regulation of expression is disrupted, e.g. cells in which p53 is mutated. The first promoter may be one which is unregulated in tumor cells, for example the Hsp70 promoter which is upregulated in mutant p53 tumor cells. A suitable antitumor agent in thymidine kinase.

19 Claims, 14 Drawing Sheets

OTHER PUBLICATIONS

Figure 3:
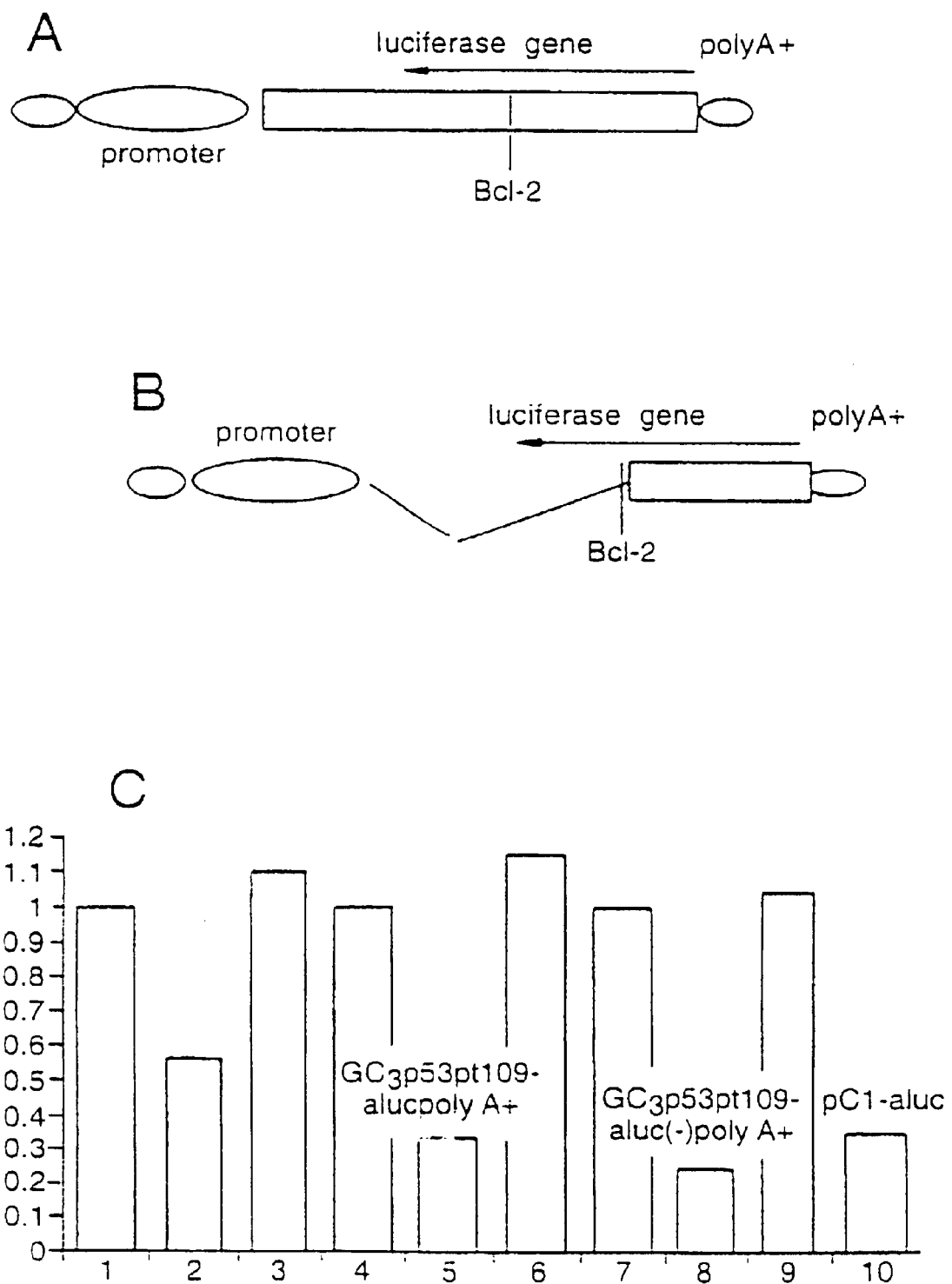

Pescini, Rosanna et al. (1994) "Inducible Inhibition of Eukaryotic Gene Expression", Biochemical and Biophysical Research Communications, vol. 202, No. 3, pp. 1664–1667.

Pitts, John D. (1994) "Cancer Gene Therapy: A bystander Effect Using The Gap Junctional Pathway" Molecular Carcinogenesis, vol. 11 pp 127–130.

Selvakumaran, Muthu et al. (1994) "Immediate Early Up–Regulation of bax Expression by p53 But Not TGFβ1: A Paradigm For Distinct Apoptotic Pathways", Oncogene, vol. 9, No. 6, pp. 1791–1798.

Shiio, Yuzuru et al. (1993) "Indentification of A DNA Element That Can Enhance p53–Mediated Transactivation", Oncogene, vol. 8, NO. 8, pp. 2059–2065.

Takebe, Yutaka et al. (1988) "SRα Promoter: An Efficient And Versatile Mammalian cDNA Expression System Composed of the Simian Virus 40 Early promoter and the R–U5 Segment of Human T–Cell Leukemia Virus Type 1 Long Terminal Repeat", Molecular and Cellular Biology, vol. 8, No. 1, pp. 466–472.

Tsutsumi–Ishii, Yuko et al. (1995) "Response of Heat Shock Element Within The Human HSP70 Promoter To Mutated p53 Genes", Cell Growth & Differentiation, vol. 6, No. 1, pp. 1–8.

* cited by examiner

Fig.1.
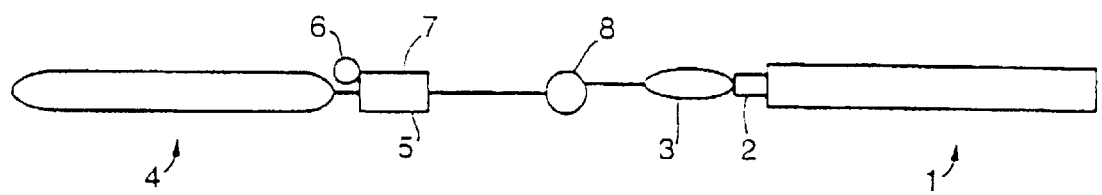
Fig.2.
A
HSVtk promoter
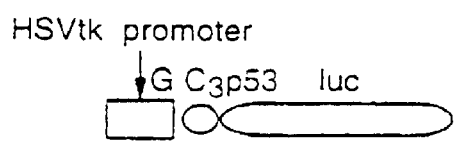
HSVtk promoter
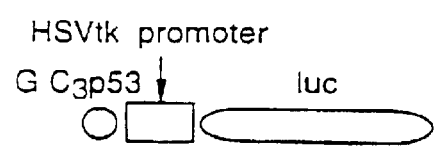
B
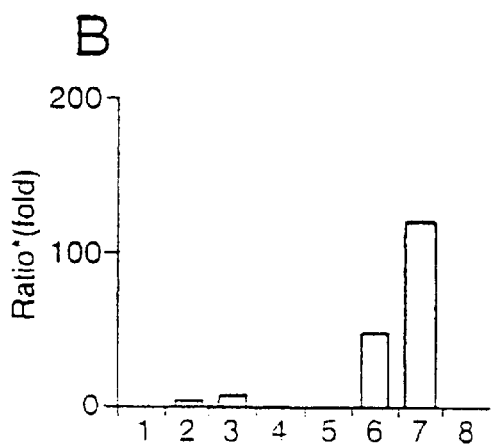
C
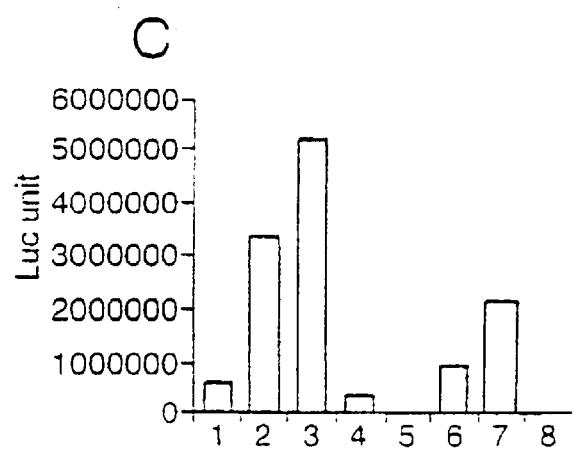

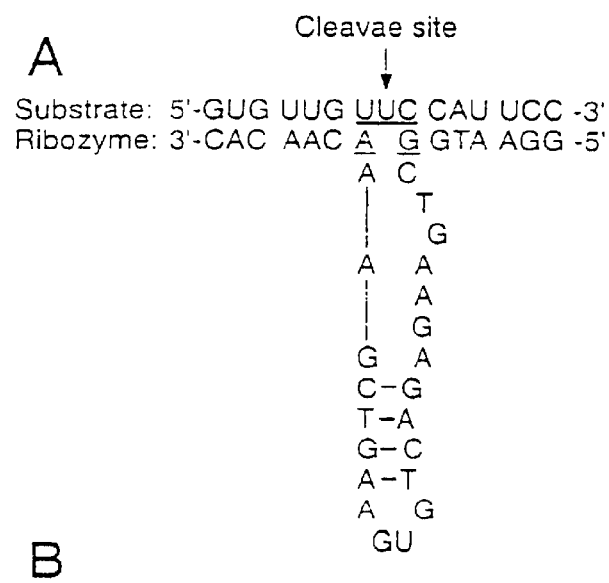
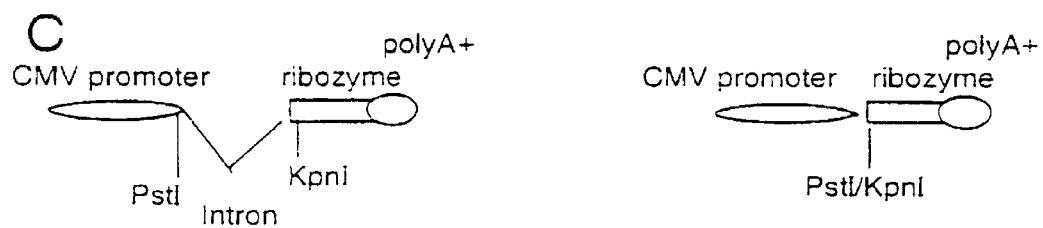
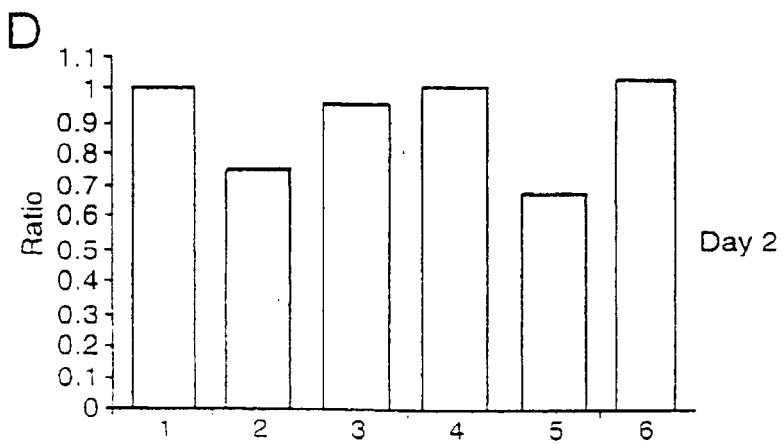
Fig.4.

Fig. 5.
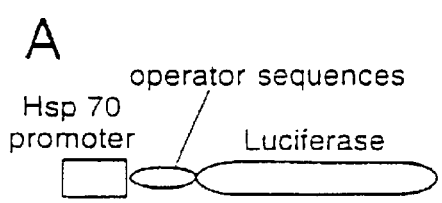
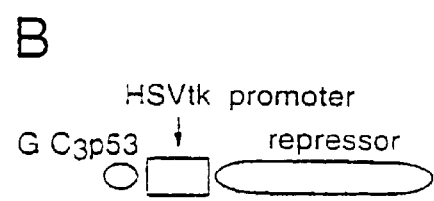
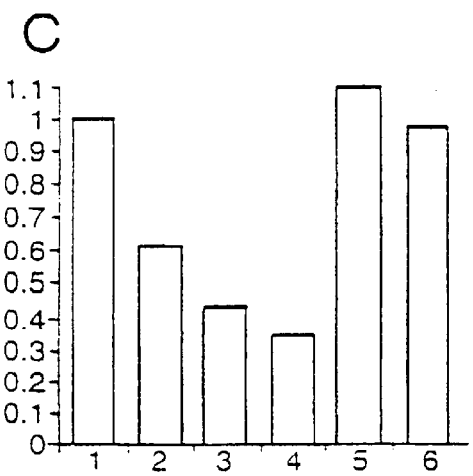
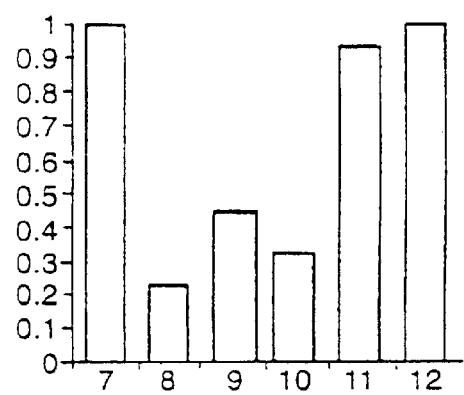

Fig. 6.
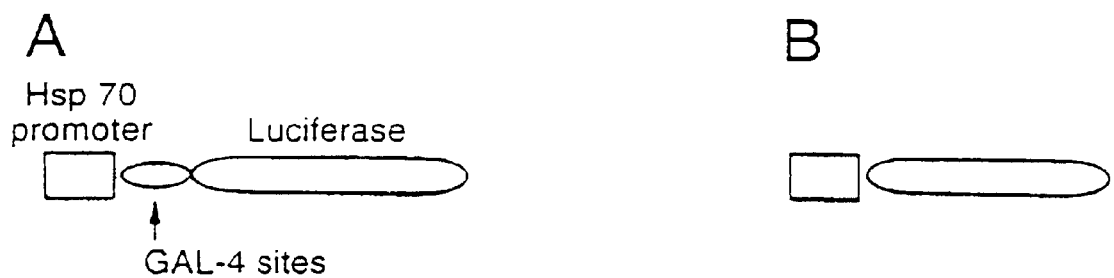
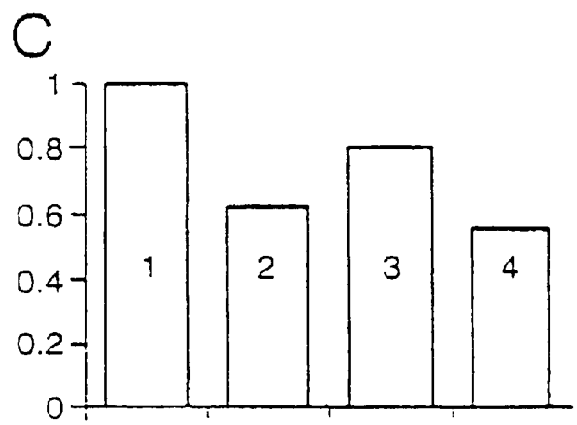
Fig. 7.
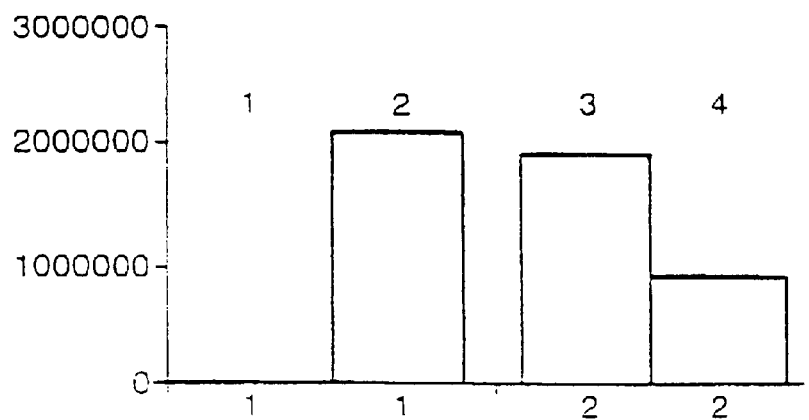

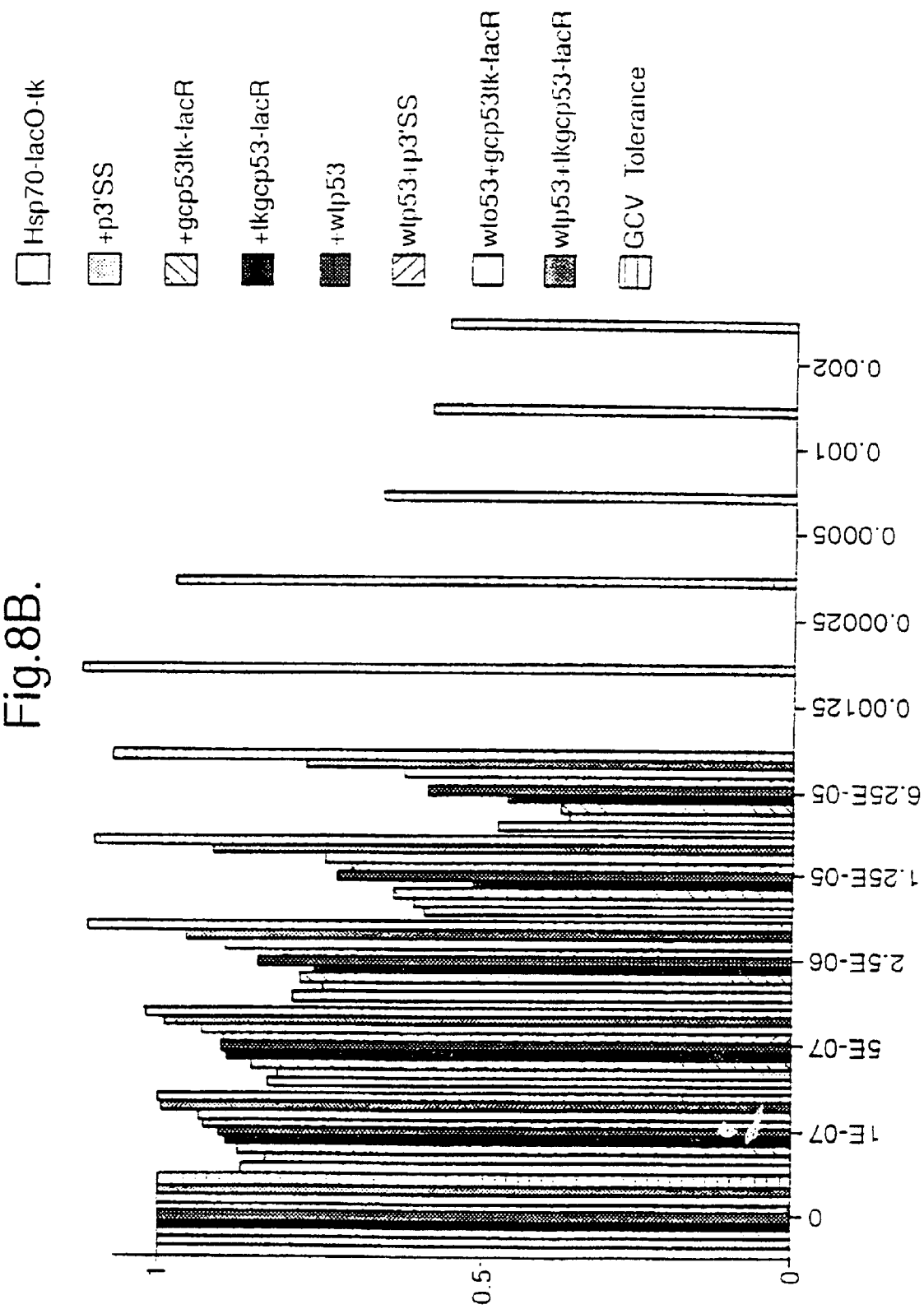

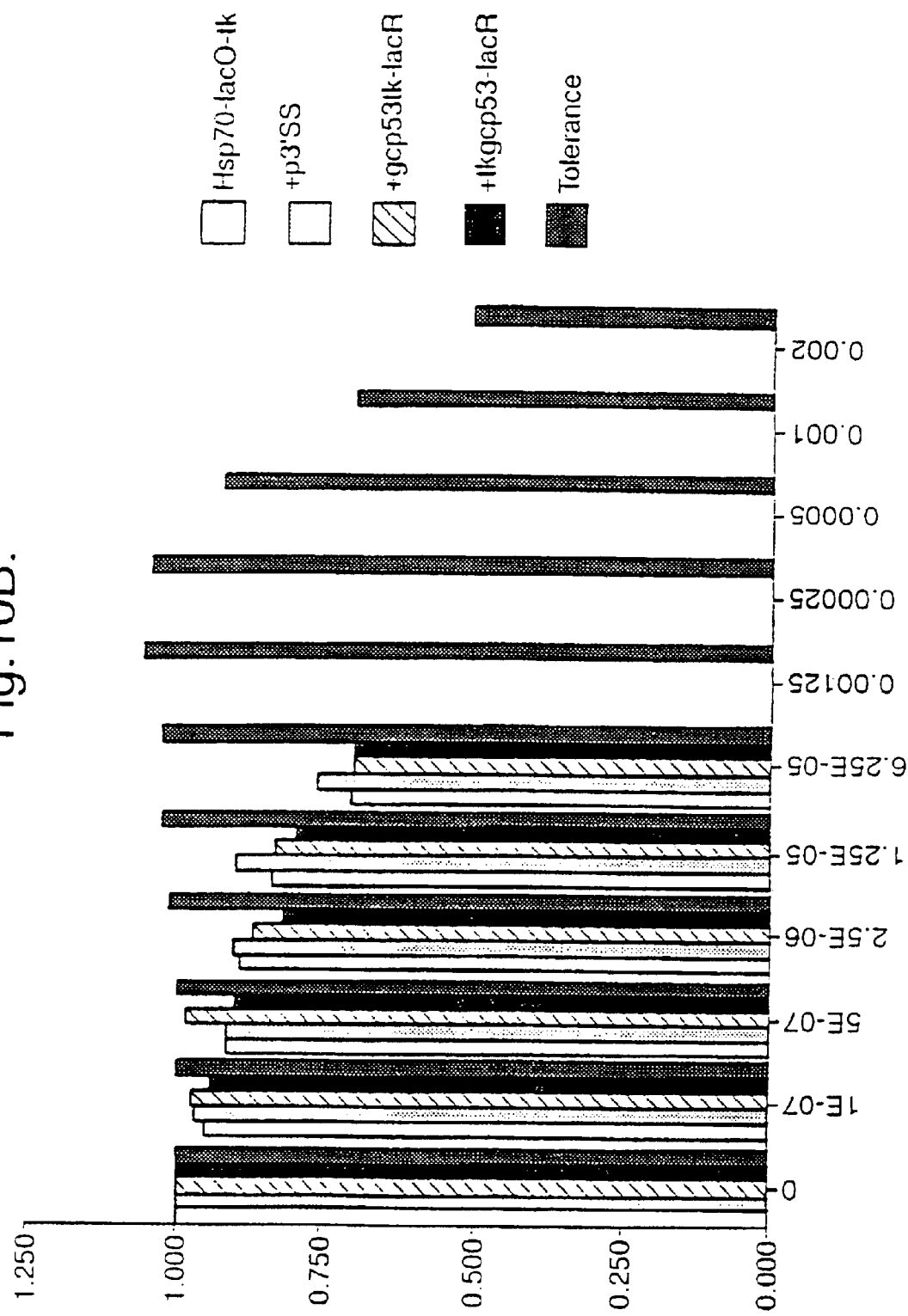

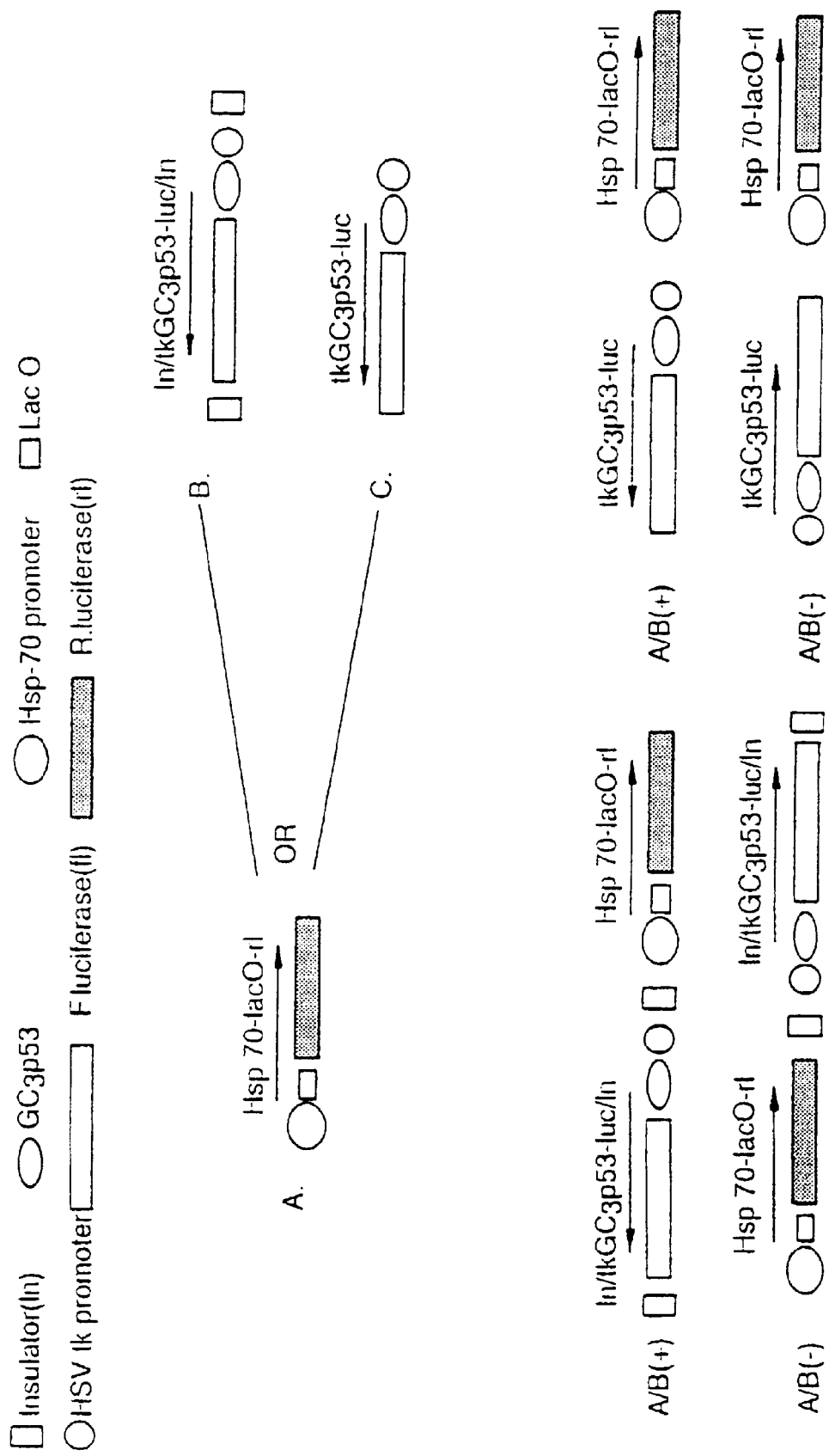

Fig.12.
A
```
    1   2   3   4   5   6   7   8   9
 1  /                       /
 2  /                           /
 3      /                   /
 4      /                       /
 5          /               /
 6          /                   /
 7              /           /
 8              /               /
 9                  /   /   /
10                  /   /       /
11                  /   /           /
12                  /   /           /
```
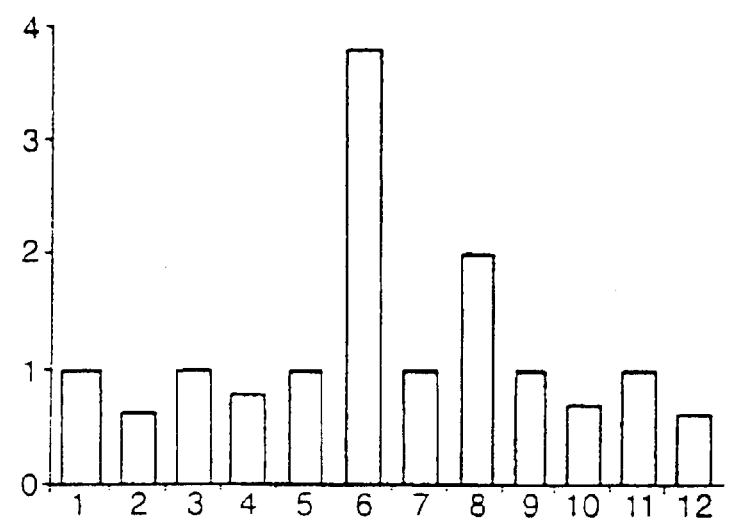
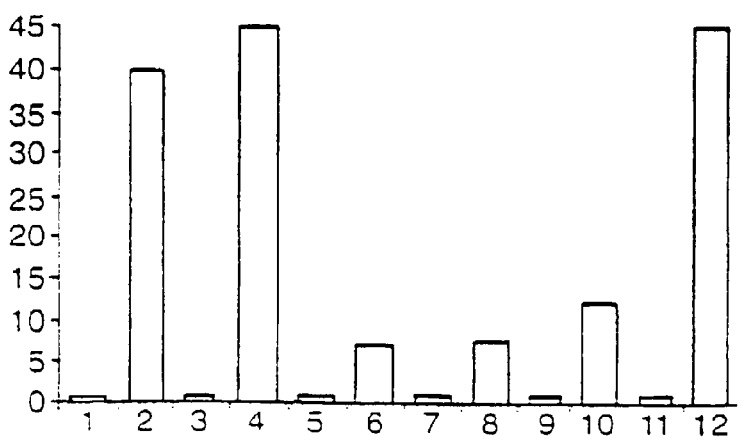

Fig.13.
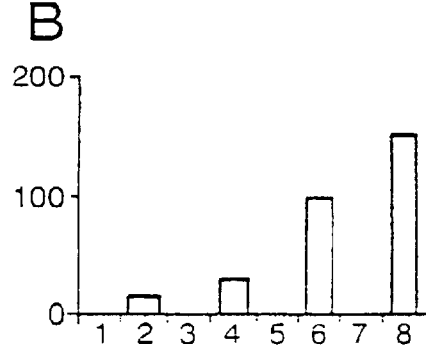
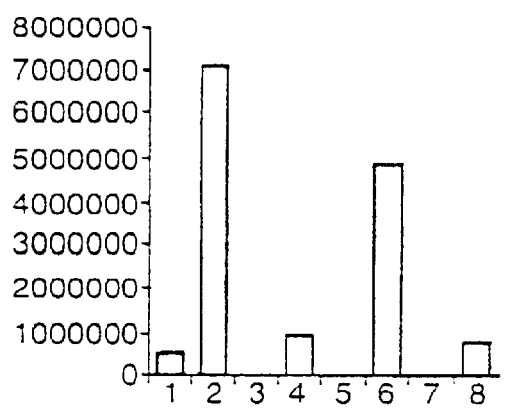
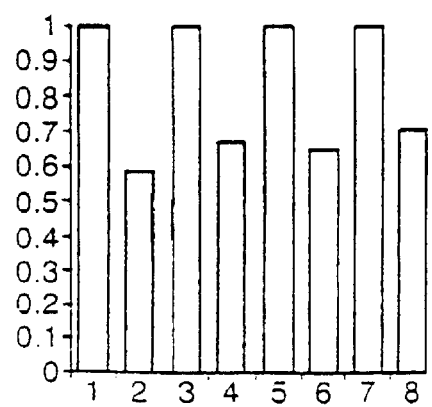

ANTITUMOUR VECTOR CONSTRUCTS AND METHODS

The present invention relates to the control of proliferation of tumour cells, preferably by killing those cells. More particularly it relates to methods and means for selectively attacking tumour cells with cytotoxic or antiproliferative agents (herein generally referred to as antitumour agents).

The concept of targeting antitumour agents to tumour cells has been considered and investigated over a number of years. Such approaches include for example the use of supposedly tumour-specific antibodies or ligands as carriers for cytotoxic agents, but this has problems, such as finding antigens or ligand receptors which occur on all tumour cells and virtually not at all on normal cells; also the problem of physically getting the conjugate to the target tumour cells.

A variety of gene therapy strategies have been proposed, some of which are currently in clinical trails. These include ex-vivo introduction of cytokines into explanted tumour cells or into tumour infiltrating lymphocytes (TIL) followed by reintroduction of these cells into patients, in the hope of stimulating tumour recognition and elimination by the immune system [1].

A complementary approach has been to introduce pro-drug activating enzymes, the most common of which is the herpes simplex virus thymidine kinase gene (HSVTK) which can metabolise the pro-drug, Ganciclovir, to a cytotoxic metabolite capable of killing the host cell [2]. A major advantage of this strategy is that the so called "bystander effect" limits the requirement to target the gene to all of the tumour cells. Using the TK gene, the cytotoxic drug which is generated can pass through gap junctional channels into surrounding cells [3], with the consequence that targeting of only 10–20% of the cells within a tumour can lead to complete tumour regression. For all proposed new cancer therapies, a similar series of problems have to be resolved, including the means of delivery of any new drug, optimisation of its uptake and stability, specificity for targeting of tumour versus normal cells and the necessity to ensure that all tumour cells are exposed to the drug.

The development of gene therapy faces exactly the same difficulties, but probably the most complicated challenge to be overcome is the ability to engineer tumour-specific expression of the targeted gene. The most commonly used method to try and circumvent this problem is to use a tissue-specific gene promoter to drive expression of the therapeutic gene in particular tumour types. For example, the tyrosinase promoter is currently being used to express TK in melanoma cells [4]. However, this promoter is active in normal melanocytes as well as in some neurons. An alternative is to utilise the promoters of genes which are upregulated in tumours such as the erbB2 gene in breast cancers [5]. This gene is, however, also expressed in normal cells and in any case its deregulation only occurs in a relatively small proportion (20–30%) of human breast, pancreatic and gastric tumours. All of the presently available systems therefore suffer from the disadvantages that specificity for normal versus tumour cells is weak and the applicability is restricted to very specific tumour types.

One objective of the present invention, therefore, is to obtain improved discrimination in the action of antitumour agents between tumour and normal cells.

In broad terms, selectivity for expression within tumour cells of the anti-tumour agent in accordance with the present invention will be effected by a combination of two approaches: (i) up-regulation of the mediating gene in tumour cells and (ii) down-regulation of the mediating gene in normal cells. Effect (i) will mediate the desired activity in and around tumour cells, while effect (ii) will reduce the extent of "leaky" expression of that activity in normal cells.

A preferred basis for this approach is centered around the p53 gene. The p53 protein is a transcriptional activator in normal cells but is present in mutant form in a substantial proportion (40–80%) of human tumours. However, mutation frequencies of p53 is likely to underestimate the actual occurence of inactivation of the p53 tumour suppressor function in tumours. Even in tumours in which the p53 sequence is wild-type, its normal function in cell cycle control, DNA repair, differentiation, genome plasticity or apoptosis [43–45] may be abrogated, for instance by interaction with cellular protein (e.g. mdm2) or oncoviral protein (e.g. SV40 T antigen, human papillomavirus E6 protein, adenovirus E1B protein, hepatitis B virus X protein, and Epstein-Barr BZLF-1 protein), or by being sequestered in the cytoplasm, where the p53 protein is non-functional.

The strategy exploits differences in the transcriptional activation and stability functions of the p53 protein between normal and tumour cells. More particularly, it utilises the dual transcriptional regulatory function of wild-type p53 (wtp53) to eliminate or minimise expression of the antitumour gene in normal cells and to enhance its expression in tumour cells. For this purpose, the strategy proposes a combination of two genetic units. In genetic unit 1, the antitumour gene is controlled by a promoter whose function is suppressed by wtp53, but is not suppressed by mutant p53 (mp53), indeed it may even be up-regulated by mp53. In genetic unit 2, a gene for down-regulating the antitumour gene in normal cells is controlled by a promoter containing the p53 binding site, and which is therefore potently up-regulated by wtp53 but not by mp53. In other words, the wtp53 in normal cells is used to up-regulate a gene which down-regulates the expression of the antitumour agent in those normal cells. The down-regulating gene may for example express antisense RNA to the antitumour gene, or a specific ribozyme for antitumour gene RNA, or a specific transcription suppressor for the antitumour gene.

By way of example, this system can be used to engineer expression in tumour cells of a pro-drug activating enzyme such as HSVTK, but will be useful for targeting of genes which enhance host anti-tumour response such as IL-2 and GMCSF, cytokines, genes which may induce tumour specific apoptosis, such as bax, or other toxins or functions such as viral replication capacity, e.g. viruses capable of replication only in tumour cells, to tumour cells.

Exemplary embodiments of dual genetic unit constructs according to the present invention are illustrated diagrammatically in FIGS. 1A and 1B, with reference to expression of HSVTK as the antitumor gene and p53-based regulation, and will be described further below.

The invention is preferably based on the p53 gene, because of its central role in tumour suppression and the differences in its function in normal and tumour cells. However, the general concept of the invention may be applicable using other genes to up-regulate the antitumour agent in tumour cells and to down-regulate it is normal cells. Since the natural tumour suppressor pathways are complex and involve many genes, at least some of them could be used in a similar fashion.

More detailed discussion of the invention in relation to p53

The most common feature of virtually all malignant tumour cells is aneuploidy. There is a great deal of evidence showing that tumour cells are genetically unstable, possibly because of the accumulation of mutations in genes which control the stability and integrity of the genome, such as p53

[6]. A consequence of such genetic changes is that tumour cells may constitutively produce signals indicating DNA damage. The main aim of the p53 aspect of this invention to engineer gene constructs which will utilise the intrinsic "DNA damage" response in tumour cells to switch on and stabilise an antitumour agent, such as a pro-drug activating enzyme.

We envisage a number of avenues by which tumour specific targetting of gene expression of an antitumour agent may be achieved. Central to the presently preferred proposal are the observations that the p53 tumour suppressor gene can act as a sensor of DNA damage or anueploidy in developing tumour cells [6]. In normal cells, p53 responds to DNA damage induced by exogenous agents initially by increasing the stability of the protein itself and/or by increasing the translatability of its mRNA [7]. Importantly, the introduction of the same mutant form of p53 into tumour cell lines showing different expression levels of endogenous p53 genes has shown that the exogenous p53 is stabilised in the same way as its endogenous counterpart [8]. In other words, the level of protein stability and expression is not simply a consequence of mutation within the coding sequence but is determined by the tumour cell microenvironment.

Stabilisation of p53 in normal cells can lead to apoptosis directly or can cause G1 arrest through the induction of genes such as p21/Waf-1 [9]. In many tumour cells these responses are abrogated, either because of deletion of p53 wild type sequences or by mutation to other conformational forms which fail to induce these responses. Interestingly, although the majority of these mutants fail to activate transcription through the recognition sequence discovered in genes such as p21/Waf-1, some of them can nevertheless stimulate transcription from some other gene promoters which are known to be upregulated in certain tumour cells, such as the MDR1 gene [10] or Hsp70 gene [11] promoters.

Since it appears extremely unlikely that the use of a single tissue-specific or tumour-selective gene promoter to drive eg TK expression will give sufficient discrimination between normal and tumour-cells, the present invention proposes the use of both altered transcriptional control by wild-type and mutant p53 and altered translation or stability of the p53 protein itself to control the expression of eg HSVTK for the purpose of gene therapy. Such transcriptional control and such translational or stability control may be used individually or in combination. The constructs are tested initially in vitro, but will ultimately be rigorously tested for tumour specificity in vivo by using human tumour xenografts in nude mice and transgenic mice.

For convenience, initial studies are carried out with marker genes such as luciferase, as well as with HSVTK (pro-drug activating enzyme), but these will then be extended to other systems. The advantages of the proposed system include wide applicability to a range of tumour cell types and the ability to extend the system to include tumour specific expression of other potentially therapeutic genes in addition to pro-drug activating enzymes, eg genes which enhance host anti-tumour response, such as IL-2, GMCSF, cytokines, genes which may induce tumour specific apoptosis, such as a bax, toxins or genes which control viral replication capacity, for instance viruses capable of replicating only in tumour cells.

p53 mediated transcriptional control

Wild-type p53 protein contains at least 4 functional domains, one of which (residues 102–290) binds to two copies of the consensus sequence 5'PuPuPuC(A/T)(A/T) GPyPyPY-3' (SEQ ID NO:1) [12–15]. GCCC+a dimer of the consensus sequence has been used herein, as discussed below, and is known as $GC_3p53$ (the sequence exemplified using $GC_3(GGACTTGCCT)_2$ (SEQ ID NO:2). Transactivation through this sequence increases the level of transcription of a number of cellular genes, some of which play major roles in the negative regulation of cell proliferation or in triggering programmed cell death (apoptosis).

A p53 consensus sequence is present within the 5' region of the gene encoding the p21/Waf-1 cdk inhibitor, which can arrest the cell cycle in the late G1 phase [16] and inhibits the function of proliferating cell nuclear antigen (PCNA), a regulatory subunit of DNA polymerase delta [17].

Up-regulation of the gene encoding the Bax protein, which promotes apoptosis by inhibition of Bcl-2, has also been reported to be induced by wild-type p53 [18].

This form of transactivation appears to be limited to promoters containing the p53 consensus binding site, whereas the promoters of a number of other cellular genes including Bcl-2 [19], PCNA [20, 21], the multi-drug resistance gene MDR1 [10] and the HSP70 genes [11] are negatively regulated by wild-type p53. The latter effect probably involves complex formation of wild-type p53 with various components of the basal transcription machinery [22–25].

Most of the mutations in the p53 gene lead to abrogation of the sequence-specific transcriptional activating function and prevent the suppression of tumour cell growth in vitro. This has been attributed to dominant negative suppression of wild-type p53 function in heterozygous cells, but in some cases gain of function properties have been ascribed to some mutant forms [26]. This gain of function could be due to the reported ability of some mutant p53 alleles to transactivate promoters which are normally suppressed by wild-type p53 [11]. For example, both PCNA and MDR1 promoters, in addition to the HSP70 promoter, have been reported to be transactivated by several mutant p53 genes [20, 27].

Gene promoters which exhibit these opposite transcriptional responses to wild-type and mutant p53 may be extremely useful for tumour specific gene targeting. A construct driven by either the MDR1 or HSP70 promoters would be expected to be expressed at high levels in tumour cells carrying mutant p53 genes but suppressed in normal cells, expressing wild-type p53. However, although there may be some selective activity in the use of these promoters, complete discrimination between normal and tumour cells would not be expected. We therefore incorporate an additional control element designed to suppress expression specifically in normal cells (as illustrated by way of example of FIG. 1). The HSP70 promoter is a good choice of promoter for the Type I unit because its overall strength is relatively moderate, which makes it more likely that complete suppression can be achieved in normal cells with wild-type p53.

The initial constructs comprise two separate genetic units. The HSVTK gene is driven by a promoter (type I promoter) which is not suppressed by, and may even be stimulated by, mutant p53 but is suppressed by wild-type p53 (eg the HPS70, MDR1 or PCNA promoters). The second genetic unit is designed to suppress any leaky expression of the TK gene in normal cells. The promoter for this unit (type II promoter) contains the p53 consensus binding sequence, which is only activated by wild-type p53, within the context of a minimal promoter comprising a transcriptional start site and TATA Box. The p53 binding sequence may be included upstream of the minimal promoter or downstream. Experimental results included herein show that in one exemplary system better results are achieved with the p53 binding sequence downstream from the promoter in genetic unit II.

Apart from p53, other genes associated with the tumour suppression pathway may be utilised in the present invention. For example, the p16 INK4A gene has a tumour suppressor function. It inhibits phosphorylation of Rb protein, which in turn negatively regulates the p16 promoter. Many tumours have Rb or p16 deletions, but not both, so that Rb-negative tumours tend to have high p16 levels. The p16 promoter should therefore be strongly up-regulated in Rb-negative tumours, and could be used as the type I promoter in our dual construct.

Various means of suppressing leaky transcription in normal cells may be employed and three different approaches have been considered experimentally (results provided below):

(i) One approach employs an antisense construct (e.g. for HSVTK) driven by the type II promoter (e.g. p53 responsive). No antisense transcript should therefore be produced in tumours harbouring only mutant p53, but this construct should be transcriptionally activated within normal cells and lead to down-regulation of any functional TK transcript driven by the type I promoter. It should be noted that even although normal cells express only very low levels of wild-type p53, the introduction of gene constructs by transfection has been shown to induce expression of detectable wild-type p53 [28]. Such induction would therefore help to improve discrimination between normal and tumour cells using the construct shown in FIG. 1. Low dose radiation, which would be expected to induce wt p53 in normal but not tumour cells, may also improve discrimination.

(ii) Another approach to suppressing the level of activity of a polypeptide such as TK in normal cells involves the use of a specific ribozyme [29] designed to complex with and cleave the target (e.g. TK) mRNA.

(iii) A third approach uses a sequence-specific transcriptional suppressor. Several such transcriptional suppressors have been characterised. Experiments may include use of the binding domain of the yeast Gal-4 transcription factor and the suppression domain of the Drosophila even-skipped protein [30] under the control of the type II promoter to suppress expression by means of a tandem repeat of the Gal-4 target sequence [31] cloned into the type I promoter. Further experiments are described below, e.g. involving lacI and tet repressor systems.

A combination of two or more such approaches may be utilised. However, the most appropriate approach may vary according to the antitumour gene being expressed.

It antisense or ribozyme technology is employed, the sequence expressed by the Type II unit must be tailored to the sequence expressed by the Type I unit, adding a level of complexity to experimentation. In contrast, the use of a transcriptional suppressor has the advantage of allowing the construction of a "universal cassette" into which different coding sequences, e.g. anti-tumour or marker genes, may be inserted under the control of the Type I promoter without there being a need for tailoring of the Type II unit.

In experimental optimisation of the antitumour system of the present invention, initially the type I and type II promoter constructs may be tested individually, to assess the magnitude of the effects which can be generated. Co-transfections may then be carried out to assess the combined effects of both constructs in determining overall expression levels of a reporter gene such as luciferase in the presence of wild-type or mutant p53. Finally, both genetic units may be incorporated into a single construct in either a head-to-head (as in FIG. 1), tail-to-tail or head-to-tail arrangement, in the latter case having the type II promoter upstream of the type I promoter, or vice versa. If it is observed that there is transcriptional or enhancer interference between the two constructs, this may be overcome by altering the relative distance between and/or orientation of the units, and/or by linearisation of the construct, and/or (see FIG. 1) by the introduction of so-called interruptor (insulator) sequences, which have been characterised for example in Drosophila [32,33] and chicken [34, 42] systems, and shown to prevent interactions between enhancer elements in adjacent transcription units.

p53-mediated stabilisation

An aspect of the present invention provides a composition wherein a first gene of which the expression product is desired to be stabilised in tumour cells is provided as a fusion with a sequence encoding p53 protein or a fragment of p53 protein which is stabilised in tumour cells. Thus, a nucleic acid construct may include a gene encoding a polypeptide which is a fusion of a polypeptide of interest and p53 protein or a fragment of p53 protein which is stabilised in tumour cells.

Experimental evidence provided herein shows that stability of such fusion proteins is regulated in the same manner as wild-type p53. The fusions are stabilised in cells under conditions in which wild-type p53 is stabilised. Such constructs may be useful for targetting functional expression of a polypeptide, such as an antitumour agent, to tumour cells which either express a mutant p53 or express wild-type p53 but with abrogated function, e.g. because of abnormal location within the cell (such as in the cytoplasm—as discussed elsewhere herein).

The use of p53-mediated stabilization in targetting functional expression within tumour cells as opposed to non-tumour cells may be combined with the transcriptional control approach discussed above and below.

Compositions, cells and methods according to the present invention may be used in methods in which expression of a desired gene is targetted to tumour cells, as opposed to non-tumour cells. Such methods may be performed in vivo (e.g. by way of treatment of a human or animal body for therapeutic purposes), ex vivo (e.g. on cells removed from a human or animal body, prior to return of the cells to the body) or in vitro. Compositions and cells may be used in the manufacture of a medicament for treatment in which expression of a desired gene is targetted to tumour cells. Nucleic acid constructs may form part of a viral vector, for instance a viral vector engineered to be suitable for administration to an individual, such as a human, and preferably additionally tumour targetting.

Suitable vectors can be chosen or constructed, containing appropriate regulatory sequences, including promoter sequences, terminator fragments, polyadenylation sequences, enhancer sequences, marker genes and other sequences as appropriate. Vectors may be plasmids, viral, as appropriate. For further details see, for example, *Molecular Cloning: a Laboratory Manual:* 2nd edition, Sambrook et al., 1989, Cold Spring Harbor Laboratory Press. Many known techniques and protocols for manipulation of nucleic acid, for example in preparation of nucleic acid constructs, mutagenesis, sequencing, introduction of DNA into cells and gene expression, and analysis of proteins, are described in detail in *Short Protocols in Molecular Biology,* Second Edition, Ausubel et al. eds., John Wiley & Sons, 1992. The disclosures of Sambrook et al. and Ausubel et al., along with all other documents cited herein, are incorporated by reference.

In accordance with the present invention, compositions provided may be administered to individuals. Administration is preferably in a "therapeutically effective amount", this being sufficient to show benefit to a patient. Such benefit may be at least amelioration of at least one symptom. The actual amount administered, and rate and time-course of administration, will depend on the nature and severity of what is being treated. Prescription of treatment, eg decisions on dosage etc. is within the responsibility of general practitioners and other medical doctors.

A composition may be administered alone or in combination with other treatments, either simultaneously or sequentially dependent upon the condition to be treated.

Pharmaceutical compositions according to the present invention, and for use in accordance with the present invention, may comprise, in addition to active ingredient, a pharmaceutically acceptable excipient, carrier, buffer, stabiliser or other materials well known to those skilled in the art. Such materials should be non-toxic and should not interfere with the efficacy of the active ingredient. The precise nature of the carrier or other material will depend on the route of administration.

Experimental support for the present invention will now be described by way of illustration. Various additional aspects and embodiments of the present invention will be apparent to those skilled in the art. The following figures are referred to:

FIG. 1 shows an exemplary embodiment of constructs according to the present invention. The Type I unit (1) (right-hand side) has a suppressor binding site (2) downstream of the promoter (3); in alternative constructs the suppressor binding site in the Type I unit is upstream of the promoter. The suppressor binding site may be absent if the Type II unit (4) expresses antisense RNA or a ribozyme. In the Type II promoter (5), the p53 binding site (GC3p53) (6) may be upstream or downstream of the minimal promoter element (7). The insulators (8) indicated as being between the Type I and Type II units may not be necessary.

FIG. 2 shows schematic representations of two constructs (FIG. 2A) comprising a luciferase encoding sequence under the control of a HSV tk promoter (−109 to +52) and a GC3p53 sequence. In GC3p53tk-luc (right-hand side of the figure), the GC3p53 sequence is upstream of the tk promoter element; in tkGC3p53-luc (left-hand side of the figure) it is downstream. The results of transfection assays are shown in Table 1; 1 μg tkGC3p53-luc (lanes 1–4) or GC3p53tk-luc (lanes 5–8) was co-transfected with 1 μg pCI (an empty expression vector having a CMV promoter), 0.5 and 1.5 μg of the wtp53 and 1 μg mutant p53 (mt3:$_{143}$ala-val) constructs in which the p53 gene is under control of the MCV promoter into K562 cells. FIG. 2B shows the ratio of the luciferase activity in extracts from the transfected cells with either wtp53 or mtp53, over that with pCI (as shown in the "ratio" column of Table 1). FIG. 2C shows the actual luciferase activity. The conclusion is that the tkGC3p53 element shows higher background activity in the absence of wild type p53 than the GC3p53tk construct, but the latter shows much stronger relative inducibility by p53 co-transfection.

FIG. 3 shows (FIG. 3A) a schematic representation of constructs with comprise a full length antisense luciferase coding sequence under the control of the CMV promoter (construct pCV-aluc-poly A+) or a GC3p53-Tk promoter (construct GC3p53pt109-aluc-poly A+), and (FIG. 3B) a schematic representation of construct GC3p53pt109-aluc(−) poly A+, which comprises in antisense orientation part of the luciferase coding sequence (=582 −+1) under the control of the GC3p53-Tk promoter. Table 2 shows the results of transfection assays in the presence and absence of wild-type and mutant p53. 1 μg HSp70-luc was co-transfected with the control vector pCI (lanes 1, 4 and 7), wtp53 (lanes 2, 5 and 8) or mt 143 (lanes 3, 6 and 9). GC3p53pt109-aluc-poly A+, GC3p53pt109-aluc-(−)poly A+ and pCI-aluc were also transfected into k562 cells (lanes 4–6, 7–9, and 10, respectively). After a two-day culture, the luciferase activity was measured and the ratios over lane 1 (for lanes 1–3, 10), lane 4 (for lanes 4–6) and lane 7 (for lanes 7–9) were used to illustrate the suppressing effects of the wtp53 alone and the antisense combined. This is also illustrated in FIG. 3C in the form of a plot.

FIG. 4 shows: FIG. 4A—the sequence of a ribozyme designed to target a 15 base pair substrate sequence within the luciferase gene (SEQ ID NO:5), and the substrate sequence (from 716–731 of the luc gene of pGL3-basic) (SEQ ID NO:4); FIG. 4B—the sequence of two complementary oligonucleotides, lucRa (SEQ ID NO:6) and lucRb (SEQ ID NO:7). The reannealed oligos were cloned into SalI/SmaI sites of the expression vector pCI. FIG. 4C—a schematic representation of constructs pCI-luc-ribo(9) (left-hand side of the figure), comprising the ribozyme under the control of a CMV promoter and including an intron sequence, and pCI-luc-ribo*(2) (right-hand side of the figure), which is an intron-deleted derivative of the former construct, by PstI/KpnI digestion followed by self-ligation/transfection into bacteria; Table 3 shows results of transfection assays with the constructs: 1 μg Hsp70-luc, in which the luciferase gene is under the control of human Hsp70 promoter (from −117 to +26), or was co-transfected with 1 or 2 μg pCI (lanes 1 and 4), 1 or 2 μg pCI-luc-ribo(9) (lanes 2 and 5, and 1 or 2 μg pCI-luc-ribo*(2) (lanes 3 and 6). the luciferase activity was measured after two days' culture. The effect of the ribozyme over the expression of luciferase is presented as the ratio of the luciferase activity of each transfectant over the transfectants with pCI DNA (column headed "ratio"). This ratio is also shown in plot form in FIG. 4D. Background references for ribozyme include Kashani-Sabet and Scanlon, 1995 *Cancer Gene Therapy*, 2(3):213–223, and Mercola and Cohen, 1995, *Cancer Gene Therapy*, 2(1), 47–59.

FIG. 5: FIG. 5A shows Type I genetic unit constructs comprising a luciferase coding sequence under the control of the HSP70 promoter. In Hsp-LacO-luc (1), three copies of the Lac Operator sequence lie between the promoter and the coding sequence. In Hsp-TetO-luc (2), seven copies of the Tet Operator sequence lie between the promoter and coding sequences. FIG. 5B shows Type II genetic unit constructs comprising the GC3p53 sequence and HSV tk promoter operationally joined to a coding sequence which is in GC3p53tk-LacR (1) for the Lac Repressor and in GC3p53tk-TetR-KRAB (2) for a fusion protein comprising the DNA binding domain of the Tet Repressor and the suppression domain of the KRAB repressor of *Drosophila*. Table 4 shows the results of cotransfection experiments using the Type I and Type II genetic unit constructs of FIGS. 5A and 5B: Hsp70-lacO-luc was transfected into K562 cells with pCI (lane 1), p3'ss which encodes the lac repressor under the control of a F9-1 polyoma virus promoter (lane 2), wtp53 (lane 3), wtp53+GC3p53tklacR (lane 4), mtp53 143 (lane 5) and mtp53 (143ala>val)+GC3p53tklacR (lane 6). Hsp70-tetO7-luc was transfected into K562 cells with pCI (lane 7), CMV-tetR-KRAB (lane 8), wtp 53 (lane 9), wtp53+ GC3p53tk-tetR-KRAB (lane 10), mtp53 143 (lane 11) and mtp53+GC3p53tk-tetR-KRAB (lane 12). The luciferase activity was measured after an overnight culture and the suppression effect presented as the ratio of the luciferase activity of each transfectant (lanes 2–6 and 8–12) over that of the transfectants in lane 1 and 7, respectively. FIG. 5C shows graphically the results given in the column marked "ratio" in Table 4.

FIG. 6: FIG. 6A shows a Type I genetic unit construct comprising the luciferase coding sequence under the control of the Hsp70 promoter, with a tandem repeat of the recognition site of the yeast transcription factor GAL-4 between the coding sequence and promoter. FIG. 6B shows Type II genetic unit constructs comprising an actin promoter (ref. 30) controlling expression of a fusion protein which comprises the GLA4 DNA binding domain and (1) the BCDEF domain of *Drosophila* even-skipped transcription factor, (2) the CDEF domain of *Drosophila* even-skipped. Table 5 shows the results of transfection experiments in which 1 µg Hsp70-GAL4-luc was transfected into K562 cells with 1 µg pCI (lane 1), wtp53 (lane 2), BCDEF (lane 3) and CDEF (lane 4). The luciferase activity from each was measured after an overnight culture and the suppression effect was presented as the ratio of the luc activity lanes 2–4 over that of lane 1. FIG. 6C shows this ratio in graphical form. The Hsp70 promoter maintains its original response to p53 regulation even after insertion of the sequence containing the GAL4 recognition site. The specific suppression by the Drosophila even-skipped protein is about 40%.

FIG. 7 shows the results of experiments in which a genetic unit I (pCI-GUS) comprising GUS under the control of the CMV promoter, and a type II genetic unit (GC3P53tk-luc) comprising luciferase under the control of the tk promoter and the GC3p53 element were transfected into cells, with or without co-transfection of a construct expressing wild-type p53. (Columns 1 and 3 are Luc Series 1; columns 2 and 4 are GUS Series 2). Results are shown in Table 6.

Figure 8A:
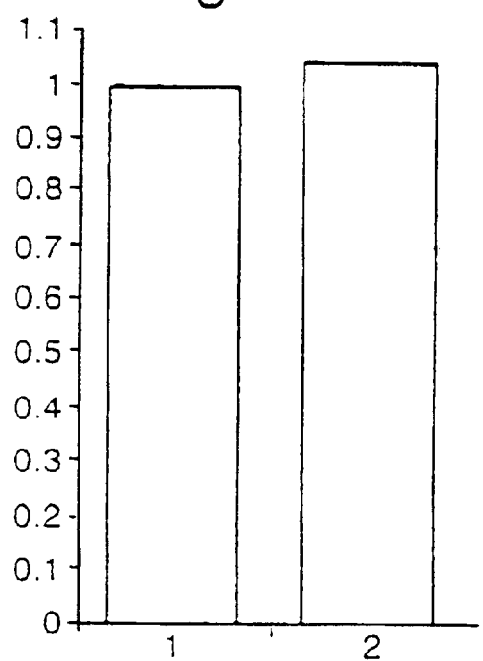

FIG. 8 shows the results of the TK-GCV cell killing assay with the Hsp70-lacO-tk system in Saos-2 cells. In FIG. 8A the ratio of luciferase activity of Saos-2 cell extracts measured on the day after transfection with (1) tk-luc or (2) GC3p53tk-luc is plotted (luciferase activity of the extracts by GC3p53tk-luc over that by tk-luc). FIG. 8B shows the ratio of the mean of absorbance at 570 nm of cells transfected with various constructs and treated with various concentrations of GCV over the no-GCV control was calculated and plotted against GCV concentration (M) (as indicated in this figure).

Figure 9A:
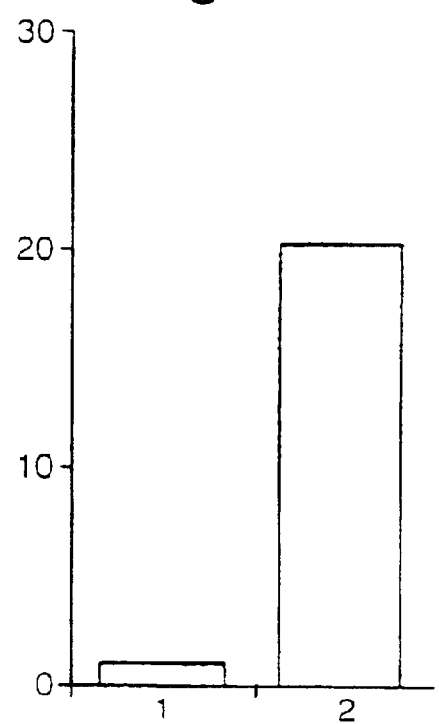
Figure 9B:
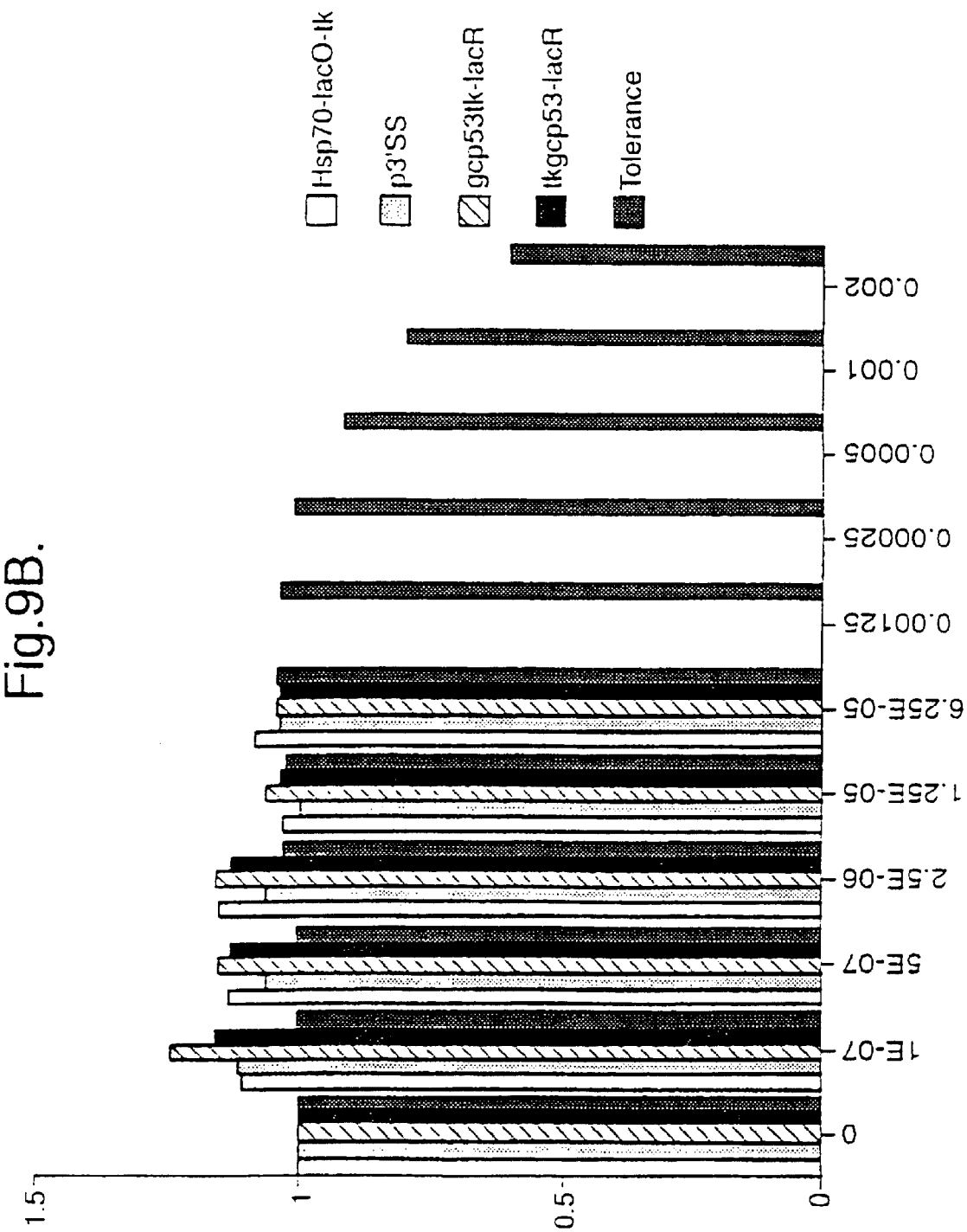

FIG. 9 shows the TK-GCV cell killing assay with the Hsp70-lacO-tk system in MCF-7 cells. In FIG. 9A the ratio of luciferase activity of MCF-7 cell extracts measured on the day after transfection with (1) tk-luc or (2) GC3p53tk-luc is plotted (luciferase activity of the extracts by GC3p53-tk-luc over that by tk-luc). FIG. 9B shows the ratio of the mean of absorbance at 570 nm of cells transfected with various constructs and treated with various concentrations of GCV over the n-GCV control was calculated and plotted against GCV concentration (M) (as indicated in this figure).

Figure 10A:
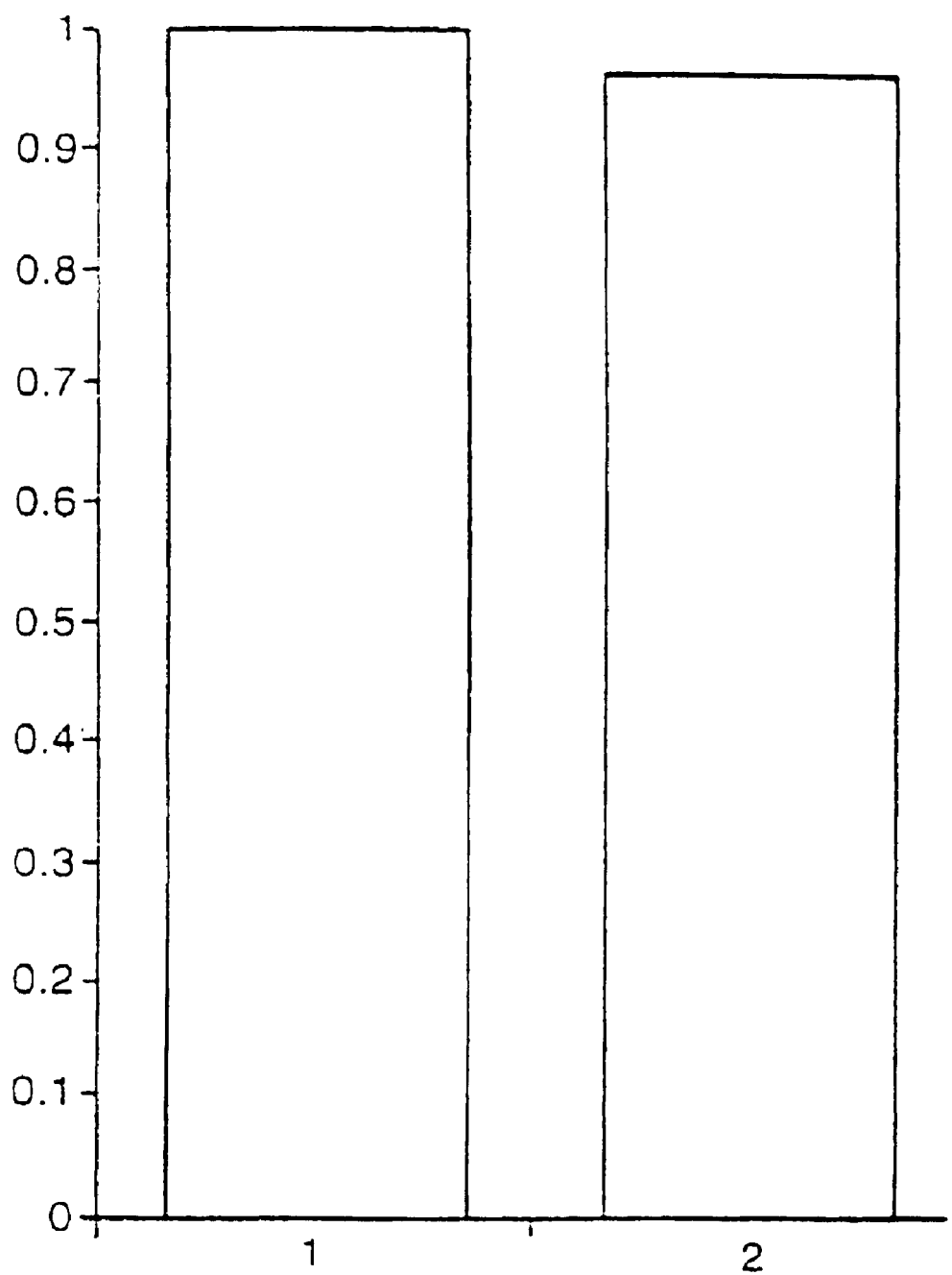

FIG. 10 shows the TK-GCV cell killing assay with the Hsp70-lacO-tk system in MHG-U1 cells. In FIG. 10A the ratio of luciferase activity of MHG-U1 cell extracts measured on the day after transfection with (1) tk-luc or (2) GC3p53tk-luc is plotted (luciferase activity of the extracts by GC3p53-tk-luc over that by tk-luc). FIG. 10B shows the ratio of the mean of absorbance at 570 nm of cells transfected with various constructs and treated with various concentrations of GCV over the no-GCV control was calculated and plotted against GCV concentration (M) (as indicated in this figure).

FIG. 11 illustrates constructs used in assays employing linked Genetic Units I and II. FIG. 11A illustrates construct Hsp70-lacO-r1. FIG. 11B illustrates construct ln/tkGC3p53-luc/ln. FIG. 11C illustrates construct tkGC3p53-luc. FIG. 11D illustrates constructs A/B(+), A/B(−), A/C(+) and A/C (−).

FIG. 12 provides information on experiments employing constructs illustrated in FIG. 11, i.e. dual control constructs containing both Genetic Units I and II. FIG. 12A provides a key to the constructs employed in the experiments whose results are shown in FIGS. 12B and 12C. The x-axis numbers in FIGS. 12B and 12C are given down the side of FIG. 12A, indicating which combination of vectors 1–9 (across the top of FIG. 12A) were employed in the experiments whose results are shown in FIGS. 12B and 12C. The vectors were as follows: 1-A/B(+):2 µg/2 µl; 2-A/B(−):2 µg/1.97 µl; 3-A/C(+):2 µg/2.19 µl; 4-A/C(−);2 µg/3.6 µl/ 5-Hsp70-lacO-rl: 1 µg/0.7 µl; 6-tkGC$_3$p53-luc:1 µg/1.1 µl; 7-pCI:1 1µg/0.4 µl; 8-pCMVwtp53:1 µg/1.1 µl; 9-In/ tkGC$_3$p53-luc/In:1 µg/0.517 µl.

FIG. 12B shows the ratio of the Renilla luciferase activity of extracts of cells co-transfected with wtp53 over those co-transfected with the p53-vector pCI. FIG. 12C shows the ratio of the firstly luciferase activity of extracts of the cells co-transfected with wtp53 over those co-transfected with pCI.

FIG. 13 provides information on experiments performed using contructs as follows: 1-tkGC$_3$p53-luc:1 µg/1.76 µl; 2-In/tkGC$_3$p53-luc/In(3)+:1 µg/0.74 µl; 3-GC$_3$p53tk-luc:1 µg/1.1 µl; 4-In/GC$_3$p53tk-luc/In(4)+:1 µg/0.517 µl; 5-pCMVwtp53:1 µg/1.1 µl; 6-pCl:1 µg/0.4 µl; 7-Hsp70- lacO-rl(2):1 µg/0.73 µl. Details of the combinations 1–8 of constructs 1–7 used in the experiments for which results are given in FIGS. 13B, 13C and 13D, are given in FIG. 13A. K562 cells were transfected with the combinations of constructs and both Firefly and Renillar luciferase activities were measured. FIG. 13B shows the ratio of the Firefly luciferase activity between each pair of the transfection. The actual Firefly luciferase activity of the corresponding extracts are shown in FIG. 13C. FIG. 13D shows the down-regulation effect of wtp53 on the Hsp70 promoter in the Hsp70-lacO-rf system.

FIG. 14 shows results of experiments on p53 stabilisation in tumour cells.

Figure 14A:
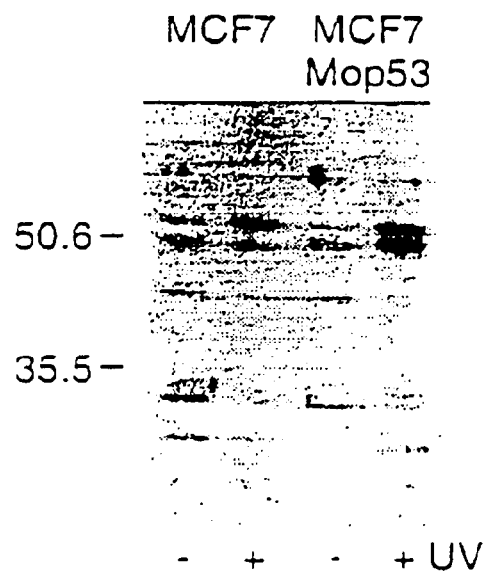

FIG. 14A shows a Western blot of cell lysates with polyclonal rabbit serum that specifically detects mouse and human p53 protein. The endogenous p53 protein of the MCF7 tumour cell line is unstable and barely detectable (first lane of gel) unless the cells are irradiated with UV light, when p53 becomes stable (second lane). A new line of MCF7 cells was isolated which also express a mouse p53 (from plasmid Mop53His169). The endogenous human and the introduced mouse p53 protein (which can be differentiated from human p53 by its slightly higher mobility on the gel) are again barely detectable (third lane) unless the cells are irradiated with UV light (fourth lane) when both proteins become stable.

Figure 14B:
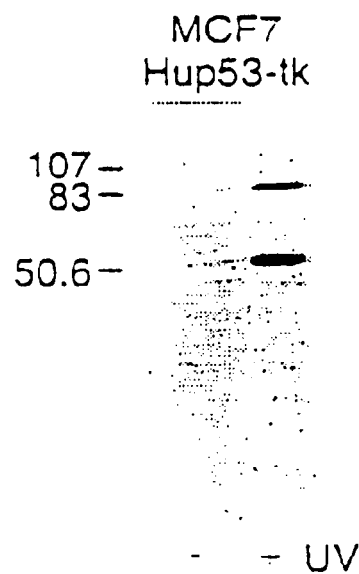

FIG. 14B shows a Western blot of cell lysates with polyclonal rabbit serum that specifically detects human p53 protein. A new line of MCF7 cells containing pCDNA3 Hup53-tk was isolated. Plasmid pCDNA3 Hup53-tk expresses a fusion protein consisting of full length p53 fused to the N-terminus and of full length thymidine kinase. The endogenous normal human p53 and the fusion protein are again barely detectable (first lane) unless the cells are irradiated with UV light (second lane) when both the normal p53 and the fusion protein become stable. Regulation of stability has therefore been conferred on the tk protein by expressing it as a fusion protein with p53 protein.

All documents mentioned in this document are incorporated by reference.

Results on transcriptional control

Preliminary experiments

A series of constructs have been prepared and used in transfection assays with a luciferase reporter gene to test the feasibility of the proposed approaches.

i. Firstly, using a transient co-transfection assay into a p53-minus human leukaemia cell line, K562, we have reproduced the down-regulation effect of wtp53 on the promoter function of four different promoters: the SV40 early promoter, the HSV-thymidine kinase (tk) promoter (−109 to +52) or (−81 to +52), the CMV promoter and the human HSP70 promoter. Three mutant p53 genes (143, 248 and 216) tested had lost this suppression (down-regulation) function.

For example, using the HSP70 promoter construct taking as unity the level of luciferase reporter gene expression obtained from 1 $\mu$g of vector, a wtp53 dosage of 0.25 $\mu$g reduced the expression to 0.708, while a dosage of 0.8 $\mu$g reduced it to 0.302. On the other hand, 1 $\mu$of a mutant p53 (mt143) increased the expression level to 1.11.

ii. Secondly, the GC3 element of the p53 recognition sequence element (GC3p53) in the human Rb promoter [35] was cloned upstream of the HSV-tk promoter (−109 to +52) or (−81 to +52), as well as the mouse fos minimal promoter (−56 to +166). Co-transfection with wtp53 was found to enhance the reporter gene expression dramatically by a factor of approximately 350-, 90- and 30-fold, respectively. None of the three mutant p53 genes had a detectable enhancing effect.

The dosage effect on the transactivation function of wtp53 was tested, using the GC3p53 construct with the HSV-tk promoter (−109 to +52). Taking the baseline level of expression as unity using 1 $\mu$g vector alone (ie zero wtp53 dosage), the relative expression levels of the luciferase reporter with wtp53 dosages of 0.03 $\mu$g, 0.01 $\mu$g, 0.3 $\mu$g and 1 $\mu$g were 1.75, 32, 142.7 and 393.5 respectively. In another experiment, 0.25 $\mu$g wtp53 increased the expression level to 40.41, and 0.8 $\mu$g increased it to 104.5. On the other hand 1 $\mu$g of a mutant p53 (mt143) reduced expression to 0.54.

The GC3 element in the human Rb promoter is able to enhance p53 mediated transactivation as shown by Shiio et al [35]. Using constructions in which the CAT reporter gene is expressed from the SV40 early promoter, these authors showed that when the promoter was preceded by the p53 binding site from the Rb promoter, namely (GGACTTGCCT)$_2$ (SEQ ID NO:3), it was found to enhance CAT expression to 22 as compared with a level of 0.81 in the absence of the p53 binding site. In another construct the p53 binding site was preceded by the GC3 element, and CAT expression was enhanced to 122. On the other hand, just using a pair of GC3 element (ie without the p53 binding site) did not enhance expression over the control.

We tested the function of the GC3p53 response element in Alternative orientations, upstream of HSV-tk promoters (−81) and ('109) respectively. Although the levels of expression varied somewhat (for a 0.25 $\mu$g wtp53 dosage), the differences did not consistently favour one orientation over the other (for the (−81) promoter it was 30 in the forward orientation and 93 in the backward orientation, while for the (−109) promoter it was 41 in the forward orientation and 27 in the backward orientation). We therefore conclude that this element is probably orientation independent.

iii. Thirdly, constructs designed to express antisense fragments of the luciferase and thymidine kinase genes driven by the HSVTK promoter and the GC3p53 response element have been made and tested in transient co-transfection assays. Essentially, we used three constructs: (1) had just the HSP70 promoter expression the luciferase reporter gene; (2) had the HSV-tk (−109) promoter with the GC3p53 recognition sequence transcribing the luciferase gene in reverse orientation, followed by a polyA+ signal; (3) was similar to (2) except that it only used a 5' portion of the luciferase gene (terminating at a Bcl2 site).

Each of the three constructs was tested for luciferase expression, (a) with the vector alone at 1 $\mu$g dosage, (b) with the addition of wtp53 at 0.25 $\mu$g dosage, and (c) with the addition of mutant p53 (mt143) at 1 $\mu$g dosage. The results suggested that it is indeed possible to achieve down-regulation of luciferase expression using this anti-sense approach.

Further experiments a. Transcriptional Activity of Normal and Mutant p53 Alleles A series of different p53 mutants have been prepared and tested for activity with genetic units I and II using luciferase reporter genes. In addition to mutants $143^{ala-val}$, $216^{val-gly}$ and $248^{arg-trp}$, previously tested, the following have been tested: $175^{arg-his}$, $245^{gly-ser}$, $248^{arg-gln}$, $249^{arg-ser}$ and $273^{arg-his}$, which together represent approximately 30% of the total of 3870 mutations reported in the literature for p53 in human tumours.

Extensive transfection analyses with these mutants have been carried out and the results show that the mutants are unable to stimulate transcription through the GC3p53 consensus sequence in genetic unit II. This provides an indication that the construct should be fully functional in at least 30% of human tumours carrying p53 mutations, and probably in a significantly higher proportion.

b. Arrangement of the GC3p53 Element in Genetic Unit II

Since it was demonstrated that the GC3p53 element can function in an orientation-independent manner, it is possible that the arrangement wherein the element is placed upstream from the Type II promoter (e.g. as illustrated in FIG. 1A) might not work optimally when both units I and II are put together in one molecule.

Construct GC3p53tk-luc was made with the p53 consensus binding site upstream of the minimal tk promoter joined to a luciferase encoding sequence. Transfection assays were performed in the presence and absence of wild-type p53, as described. Results were compared with those obtained with a further construct (tkGC3p53-luc) in which the GC3p53 element was placed downstream of the tk promoter and which was made in order to minimise potential interference with the functioning of genetic unit I by the GC3p53 element in genetic element II.

The results of the transfection assays are shown in FIG. 2. The construct containing the GC3p53 element downstream of the minimal tk promoter exhibited a higher background level in the absence of wild-type p53 than the other construct. However, the induced level in the presence of wild-type p53 (530×10$^4$ luciferase units) was also considerably higher. This provides indication that more efficient suppression of expression from genetic unit I may be attained by having GC3p53 downstream from the tk promoter in genetic unit II. Additional experiments will determine the optimal configuration in a ligated dual construct.

c. The Choice of Suppression System in Unit II

Three possible types of suppressor unit out of the various approaches available in the art have been tested—antisense, ribozyme and transcriptional suppressors—and each has been shown to be effective in suppressing transcription from genetic unit I.

c(i) The Antisense Approach

Two antisense luciferase gene constructs ("Type II genetic units") have been made and tested (see FIG. 3). These comprise either a full length construct (A) or one containing only the 5' end of the gene from position +582–+1 (B). As shown in FIG. 3 the luciferase gene under the control of the Hsp70 promoter ("Type I genetic unit") was suppressed by wild type p53 down to a level corresponding to 50% of the control (compare columns 1 and 2). Co-transfection of the antisense constructs A or B with the Type I construct led to a further reduction in luciferase activity to 40% or 25% of control levels respectively (columns 5 and 8 respectively). Further controls showed that the full length antisense construct driven by a CMV promoter suppressed transcription from genetic unit I to about 37% of control levels (column 10). Mutant p53 did not activate transcription of the antisense constructs or lead to suppression of luciferase activity (compare columns 6 and 9 with 5 and 8 respectively). These results therefore indicate that expression of antisense luciferase constructs from genetic unit II can suppress the activity of genetic unit I.

c(ii) The Ribozyme Approach

A ribozyme designed to target a 15 base pair sequence from 731 to 716 within the luciferase gene has been placed under the control of a CMV promoter with or without an intron sequence (constructs shown in FIG. 4) ("Type II genetic units"). The construct with the intron was shown in co-transfection experiments to reduce the level of luciferase activity from the Hsp70 promoter ("Type I genetic unit") to 75% (1 $\mu$g, column 2) or 68% (2 $\mu$g, column 5) of control levels (column 1), whereas the construct without the intron had very little effect. Preliminary experiments suggest that this reduction effect may be increased by more prolonged incubation of the cells with the ribozyme before carrying out luciferase assays.

c(iii) The Transcriptional Suppressor Approach

Three widely used transcription suppressor elements have been tested using reporter gene constructs.

The lac operator suppressor

Three copies of the lac operator sequence were inserted downstream of the Hsp70 promoter in unit I and tested both for responsiveness to wild type p53 and to co-expression of the lac repressor. Expression of the lac repressor from a constitutive promoter reduced luciferase activity from the Hsp70-lac O-luc construct to about 60% of control values (FIG. 5, compare columns 1 and 2). Co-transfection of wt p53 and the genetic unit 2 construct containing the lac repressor reduced the luciferase activity to about 35% (column 4).

The KRAB suppressor

Seven copies of the tetracycline operator sequence were inserted downstream of the Hsp70 promoter in genetic Unit I. This promoter element maintains its responsiveness to the suppressive effects of the wild type p53 protein which causes reduction of luciferase expression to 46% of the control values. A construct comprising the GC3p53 element with the tk minimal promoter linked to the tetracycline response element/KRAB transcriptional suppressor has been prepared. This construct comprises the DNA-binding domain of the tet repressor fused with the suppression domain of the Drosophila KRAB transcription factor. The activity of this repression system was demonstrated in a co-transfection experiment of the Hsp70 tet07 luciferase construct together with the tet/KRAB repressor under the control of a strong CMV promoter (FIG. 5). This reduce the luciferase activity from the Hsp promoter to approximately 24% of control values (compare columns 7 and 8). Wild type p53 suppressed the Hsp70 tet07 luciferase construct to 46% of control values (column 9) and this was further suppressed by co-expression of the tet/KRAB fusion protein from the GC3p35 tk promoter element (to 33% -column 10). Mutant p53 on the other hand had no effect on the Hsp promoter with or without inclusion of the tet/KRAB fusion construct (columns 11 and 12). These studies clearly demonstrate the potential of KRAB to act as a transcriptional suppressor in trans of the Hsp promoter in genetic unit I.

The Gal-4 suppression system

A construct has been prepared comprising a tandem repeat of the Gal-4 recognition sequence inserted between the Hsp70 promoter and the luciferase reporter gene. As shown in FIG. 6, the promoter in this construct maintained the property of suppression by wild type p53. The promoter activity was also suppressed to 40% of control values by co-transfection of a construct comprising the Gal-4 DNA binding domain fused with the suppression domain of the Drosophila even skipped transcription factor under the control of an actin promoter.

These results demonstrate suppression of genetic unit I comprising the Hsp70 promoter, using various different transcriptional suppressor elements.

d. Dual Transcriptional Control by wtp53

We have demonstrated conclusively that within the same transfected cells genetic units I and II behave independently and predictably in response to wild-type p53, i.e. expression from genetic unit I is suppressed and expression from genetic unit II is up-regulated.

Co-expression of different reporter genes was employed to investigate further the specificity of this response. In addition to luciferase (employed in the experiments described above), four reporter genes have been characterised: $\beta$-galactosidase, secreted alkaline phosphatase, $\beta$-glucoronidase (GUS) (Clontech) and Renilla luciferase (RL) (Promega). An extensive series of transfection experiments has shown the best reporter gene to be GUS (FIG. 7) and RL (FIGS. 11–13), the other two of the four giving high levels of background activity.

FIG. 7 shows In the absence of wild-type p53 the GUS reporter activity in K562 cells was high from the CMV promoter ($>2 \times 10^6$ units, column 2), whereas luciferase activity driven by the GC3p53tk promoter was essentially at background levels ($0.019 \times 10^6$ units, column 1). Expression of wild-type p53 leads to an approximately 145-fold up-regulation of luciferase activity from the GC3p53tk promoter (column 3), together with a simultaneous down-regulation (to 0.44 of control levels) of GUS activity from the CMV promoter (a type I promoter, column 4) (see FIG. 7). This result demonstrates that genetic units I and II, when co-transfected into the same cells, respond differently to expression of wtp53. Genetic unit I is suppressed, while genetic unit II is strongly stimulated by p53.

Demonstration of p53-dependent cell killing by pro-drug activation

The experiments described above demonstrated that reporter constructs under the control of genetic units I and II behave in the predicted manner in the presence of wild-type or mutant p53. A further series of constructs was prepared in which the thymidine kinase (TK) gene was placed in genetic unit I under the control of the HSP-70 promoter. The recognition sequence for the lac repressor was inserted between the promoter and coding sequences. Genetic unit II contained the coding sequence for the lac repressor driven by the GC3p53tk or tkGC3p53 promoter elements.

These constructs were transfected into SAOS-2 cells, reported to be p53 null. Control transfection showed that the transfection efficiency for these cells is approximately 20% and that there is no detectable wild type p53 activity using a GC3p53tk luciferase reporter construct (FIG. 8A). A cell killing assay was used to determine the effect of gancyclovir treatment on SAOS-2 cells cotransfected with various combinations of constructs. Expression of TK from genetic unit I leads to death of 40–60% of cells at gancyclovir concentrations of $1.25 \times 10^{-5}$–$6.2 \times 10^{-5}$M (FIG. 8B). The observation that the level of cell killing exceeds the level expected from this efficiency of transfection demonstrates that some of the cells are being killed, as expected due to a bystander effect. Inclusion of the GC3p53tk-lacR or tkGCp53-lacR constructs did not appreciably affect this result, but in the presence of wt p53, in particular the tkGC3p53-lacR construct was able to reduce the level of cell killing to about 10–20%. Gancyclovir by itself has no effect on cell viability at these concentrations. This result demonstrates that in the presence of wt p53m considerable suppression of the effect of genetic unit I can be achieved through upregulation of the lac transcriptional repressor by the GC3p53 element.

Further tests of these constructs were carried out using cells which express endogenous normal (MCF-7 cells) or mutant (MHG-U1) p53 protein. The transfection efficiency for MCF-7 cells was higher than that observed for SAOS-2 cells, and these cells clearly had wild type p53 activity (FIG. 9A). Treatment of MCF-7 cells cotransfected with genetic units I and II did not lead to any observable cell death at a concentration of $6.25 \times 10^{-5}$M gancyclovir (FIG. 9B). This indicates that the HSP-70 promoter in genetic unit I is strongly downregulated by the wild-type endogenous p53 in MCF-7 cells. At this concentration of gancyclovir, whereas SAOS-2 cells with no wt p53 are killed to a level of at least 50% by genetic unit I (against a background transfection efficiency in this transient assay of 20%). MCF-7 cells with functional wt p53 are unaffected, even although the transfection efficiency is more than twice as high.

Further experiments were carried out with MHG-U1 cells. Although the transfection efficiency of these cells is only 1–3%, more than 25% of the cells were killed by genetic unit 1 at a concentration of $6.25 \times 10^{-5}$M gancyclovir (FIG. 10B). As expected, no effect was seen after inclusion of genetic unit 2, which is not upregulated by the mutant p53 in these cells (FIG. 10A).

The experiments and results will now be described in more detail.

Cell killing assays
Cell killing assay in Saos-2 cells

Saos-2 cells ($0.5$–$1.5 \times 10^6$ cells in 0.3 ml) were transfected with 1 µg pSV-β-gal by electroporation (320 volts/1050 µC). After an overnight incubation, the cells were fixed and stained for the expression of the β-gal [Gossler, 1994]. 400 cells were counted and the percentage of blue cells were determined and used as a measure of transfection efficiency. By this measurement, the transfection efficiency of Saos-2 cells is approximately 20%.

Saos-2 cells were transfected with 1 µg of tk-luc or GC3p53tk-luc and the luciferase activity of the cell extracts was measured on the next day. The ratio of the luciferase activity of the extracts by GC3p53tk-luc over that by tk-luc was calculated and plotted. As shown in FIG. 8A, there is no significant difference between the cell extracts transfected by either tk-luc or GC3p53tk-luc. Since p53 protein was not detectable by immunoblotting analysis with p53 antibodies (DO-1 or CMV-1), this result confirms that the p53 status of Saos-2 cells is p53–/–.

Saos-2 cells ($3 \times 10^6$ cells/0.3 ml) were transfected with 1 µg of Hsp70-lacO-tk along with 1 µg p3'SS encoding the lacR under the control of the FG-1 polyoma viral promoter, GC3p53tk-lacR or tkGC3p53-lacR. Either pCl (a CMV promoter vector control) or pCMV-wtp53 (the wtp53 gene under the control of a CMV promoter) was also included in this analysis. The MTT dye-conversion assay (Promega, [Promega, 1995]) was carried out and the ratio of the mean of absorbance at 570 nm of the cells treated with various concentrations of GCV over the no-GCV control was calculated and plotted against GCV concentration (as indicated in FIG. 8B).

The GCV tolerance profile of Saos-2 cells was determined in parallel by treating the cells with various concentrations of GCV (ranging from 0.1 µmole to 2 mM).

Cell killing assay with MCF-7 cells

MCF-7 cells ($0.5$–$1.5 \times 10^6$ cells in 0.3 ml) were transfected with 1 µg pSV-β-gal by electroporation (320 volts/1050 µC). After an overnight incubation, the cells were fixed and stained for the expression of the β-gal [Gossler, 1994]. 400 cells were counted and the percentage of blue cells was determined and used as a measure of transfection efficiency. By this measurement, the transfection efficiency of MCF-7 cells is approximately 48%.

MCF-7 cells were transfected with 1 µg of tk-luc and GC$_3$p53tk-luc, respectively, and the luciferase activity of the cell extracts was measured on the next day. The ratio of the luciferase activity of the extracts by GC$_3$p53tk-luc over that by tk-luc was calculated and plotted. As shown in FIG. 9A, there is 19 fold increase in luciferase activity in the extract transfected by GC$_3$p53tk-luc in comparison to that by tk-luc, indicating that p53 status of MCF-7 cells is wildtype.

MCF-7 cells ($3 \times 10^6$ cells/0.3 ml) were transfected with 1 µg of Hsp70-lacO-tk along with 1 µg p3'SS, GC$_3$p53tk-lacR, or tkGC$_3$p53-lacR. The MTT dye-conversion assay (Promega, [Promega, 1995]) was carried out and the ratio of the mean of absorbance at 570 $_{nm}$ of the cells treated with various concentration of GCV over the no GCV control was calculated and plotted against GCV concentration (as indicated in FIG. 9B).

The GCV tolerance profile of MCF-7 cells was determined in parallel by treating the cells with various concentrations of GCV (ranging from 0.1 µmole to 2 mM).

Cell killing assay with MHG-U1 cells

MHG-U1 cells ($0.5$–$1.5 \times 10^6$ cells in 0.4 ml) were transfected with 1 µg pSV-β-gal by electroporation (290 volts/1050 µC). After an overnight incubation, the cells were fixed and stained for the expression of the β-gal [Gossler, 1994]. 400 cells were counted and the percentage of the blue cells was determined and used as a measure of transfection efficiency. By this measurement, the transfection efficiency of MHG-U1 cells is approximately 3%.

MHG-U1 cells were transfected with 1 µg of tk-luc or GC$_3$p53tk-luc, and the luciferase activity of the cell extracts was measured on the next day. The ratio of the luciferase activity of the extracts by GC$_3$p53tk-luc over that by tk-luc was calculated and plotted. As shown in FIG. 10A, there is no significant difference between the cell extracts transfected by either tk-luc or GC$_3$p53tk-luc. Since the p53 protein was detected by immunoblotting analysis with p53 antibodies (DO-1 or CM-1), this result indicates that the p53 status of MGH-U1 cells is mutant type.

MGH-U1 cells ($3 \times 10^6$ cells/0.3 ml) were transfected with 1 µg of Hsp70-lacO-tk along with 1 µg p3'SS, GC$_3$p53tk-lacR, or tkGC$_3$p53-lacR, respectively. The dye-conversion assay (Promega, [Promega, 1995]) was carried out and the ratio of the mean of absorbance at 570 $_{nm}$ of the cells treated with various concentrations of GCV over the no GCV control was calculated and plotted against GCV concentration (as indicated in FIG. 10B).

The GCV tolerance profile of MGH-U1 cells was determined in parallel by treating the cells with various concentrations of GCV (ranging from 0.1 µmole to 2 mM).

Materials and methods for cell killing assays

Cell culture and DNA transfection:

Cell lines: Saos-2 (p53−/−, human osteogenic sarcoma cell line, ATCC HTB-85), MCF-7 (p53+/+, a human mammary adenocarcinoma), and MHG-U1 (EJ cells, human bladder carcinoma cell line, [1977] mtp53). Cells were cultured in the required media +10% calf fetal serum, to their confluence. Cells were recovered by trypsin digestion and resuspended in a single cell suspension at a concentration of $5 \times 10^6$ to $1.5 \times 10^7$ cells per ml. The optimal condition for the DNA transfection by electroporation for each cell line has been identified by a series of piloting experiments varying in voltage and volume with the pGL3 control (Promega, at which the Firefly luciferase gene is under the control of the SV-40 promoter and enhancer). The electroporation condition by which the cell extract has the highest luciferase activity is further confirmed by the β-gal staining [Gossler, 1994] of the transfected cells with the pSV-β-gal (Promega). The transfection efficiency of each cell line is presented as the percentage of the blue cells among 400 individual cells counted. The represented field was photographed with positive film and scanned and processed in computer.

Constructs:

A. Hsp70-lacO-tk

The human heat-shock gene promoter (−117 to +26) [Tsutsmi-Ishii, 1995] is amplified from the genomic DNA of the human HL-60 cells with pfu polymerase (Stratagen) and cloned at Srf I site of pCR-script™ SK(+) (Cam) (Stratagen) to create Hsp70 in sk. The 467 bp Hind III fragment from pOP13CAT (Stratagen) where three Lac operator sequences are located at an intron was cloned at Hind III site of Hsp70 in sk to create Hsp70-lacO in sk.

The coding region of the HSV thymidine kinase gene is amplified with pfu polymerase from pTKO (gift from Hein) and cloned at pSI expression vector (Promega) to create pSItk. The 1.5 kb BgI II/Bam HI fragment containing the tk gene as well as polyA+ additional signal is cloned at Sal I site of Hsp70-lacO in sk to create Hsp70-lacO-tk.

B. $GC_3p53$tk-lacR and tk$GC_3p53$-lacR

The 180 bp Sac I/BgI II fragment containing HSV tk promoter (−109 to +52) of pT-109 [Nordeen, 1988] is cloned at the Bam HI site of pCR-script™ SK(+) (Cam) (Stratagen) to create tk-sk. $GC_3p53$ element from the human Rb gene promoter [Shiio, 1993] is cloned at Eco RV site of tk-sk to create tk$GC_3p53$-sk. $GC_3p53$ element is cloned at the Sam I site of pT-109 [Nordeen, 1988] to create $GC_3p53$pT-109. And the Sal I/Bg II fragment of $GC_3p53$pT-109 is cloned at Xho I/BgI II sites of pCR-script™ SK(+) (Cam) (Stratagen) to create $GC_3p53$tk-sk.

The 1667 bp Xba I/Hind III fragment of P3'SS (Stratagen) containing the lac I gene was cloned at the Eco RV and Hind III sites of the $GC_3p53$tk-sk to create $GC_3p53$tk-lacR.

The 1.7 kb Eco RI/Sal I fragment of $GC_3p53$tk-lacR is cloned at the Hind III/Sal I sites of tk$GC_3p53$-sk to create tk$GC_3p53$-lacR.

Determination of the function status of the p53 in cell

Cells were transfected with either tk-luc {(at which the Sac I/BgI II fragment containing HSV tk promoter (−109 to +52) [Nordeen, 1988] was cloned at Sac I/Hind III sites of pGL3basic (Promega)}; or $GC_3p53$tk-luc {(at which the $GC_3p53$ element is cloned at the upstream of the tk promoter of tk-luc)}. The luciferase activity of the extract of the cells that had been transfected by $GC_3p53$tk-luc was compared with that by tk-luc. A significant enhancement of the luciferase activity of $GC_3p53$tk-luc over tk-luc is used as a criterion for the wtp53 status. Otherwise, the p53 status of the cell line is either p53−/− or mtp53 that would be distinguished by the immunoblotting with p53 specific antibodies (DO-1, from D. Lane).

TK-GCV assay

1 µg Hsp70-lacO-tk, with 1 µg of one of the following constructs: p3'SS (Stratagen), $GC_3p53$tk-lacR, and tk$GC_3p53$-lacR) was transfected into $3 \times 10^6$ either MCF-7 or MGH-U1 cells by electroporation. For Saos-2 cells, one of the additional two constructs: 1, pCI (Promega, an eukaryotic expression vector having CMV promoter) and 2, pCM-Vwtp53 (a similar construct as pCI in which the wtp53 is under the control of the CMV promoter, from B. Volgestein) were also included for transfection. After an overnight culture, the transfected cells were harvested by trypsin digestion and made up a single cell suspension at a concentration of $10^5$ cells/ml. Distribute $10^4$ cells/100 µl suspension into each well (totally 24) in the 96 well culture plate. Following a six hour culture, 100 µl medium without Ganciclovir (GCV), and with 0.2, 1, 5, 25 or 125 µmole GCV was added into the corresponding well, respectively. Each assay was carried out quadruplicately. After a 3–4 day culture, the GCV effect over the cell growth was determined by a MTT dye conversion assay (Promega, CellTitre 96™ Non-radioactive cell proliferation assay, [Promega, 1995]). In brief, 15 µl dye mixture was added into each well and cells were further cultured for four hours at 37° C. Then to each well, 100 µl solubilisation solution was added. After an overnight incubation at room temperature, the absorbance of each well at $570_{nm}$ wavelength was recorded by using an ELISA reader (Emas, Molecular Device) and the mean value of the absorbance from the four identical wells were calculated. The GCV effect on the cell growth was presented by the plot of the ratio of the mean absorbance of the cell treated with various concentration of GCV over that of the one without GCV against the GCV concentration.

The toxicity of the GCV to cells were analysed by subjecting the cells to various concentration of GCV (ranging from 0.1 µmole to 2 mM GCV at 37° C.) for 3 days. The remaining steps of the treatment were carried out as the tk-GCV assay.

e. Linkage of Genetic Units I and II

Genetic units I and II such as employed in "d" above, i.e. respectively comprising reporter genes such as GUS and luciferase are linked on a single vector construct and transfected into cells, where the tests performed in "d" above are repeated. The units are placed "head-to-head", "head-to-tail" or "tail-to-tail" and the spacing may be varied. Interruptor sequences may be employed between the two units.

The most successful vector construct arrangement, that is the arrangement found to give the best down-regulation of (e.g.) GUS activity and up-regulation of luciferase activity in the presence of wild-type p53, is tested, with the replacement of luciferase with a repressor such as the KRAB/tet fusion repressor or LacI repressor and the replacement of reporter (e.g. GUS) with tk, for tumour specific cell killing in vitro, and in vivo in nude mouse tumours.

A series of control experiments using a number of different reporter genes showed that the best combination of reporters for expression in the same transfection assays was Firefly luciferase (luc) and Renilla luciferase (rl).

The most simple test of the dual control unit was to link genetic unit I, containing the HSP 70 promoter with the lac operator driving the rl reporter, directly with genetic unit II comprising the tkGC3p53 promoter controlling luc expression (constructs A/C(+) and A/C(−), FIG. 11). Genetic unit I functioned normally in this dual construct, and showed increased luciferase activity in response to co-expression of wt p53 (FIG. 12C: compare columns 5 and 7 with 6 and 8 respectively). On the other hand, the Renilla luciferase activity from the HSP promoter in genetic unit II was also stimulated (FIG. 12B: compare columns 5 and 7 with 6 and 8 respectively). This indicated that the p53 consensus sequence in genetic unit II was having a strong enhancing effect on both promoters in the dual construct, and that insulator or interruptor sequences would be required.

Insulator sequences from the chick β-globin locus [42] were inserted at both ends of genetic unit II (either as tkGC3p53-luc or GC3p53tk-luc) (see FIG. 11), and these were tested in co-transfection assays with wt p53, with or without genetic unit I driving the rl reporter gene. The results are shown in FIG. 13.

The presence of the insulator sequences in unit II had the effect of inhibiting the tk minimal promoter both in the absence and in the presence of wt p53. However this effect was stronger in the absence of p53, with the consequence that the degree of stimulation of luciferase activity by p53 was greater than in the control constructs without the insulators (FIGS. 13B and 13C). FIG. 13D shows results which demonstrate that rl activity from genetic unit I was suppressed in the usual way by wt p53, whether or not the insulator constructs were included in the transfections.

The unit II containing the flanking insulator sequences was then directly ligated to genetic unit I driving the rl receptor, either in a head to head (construct A/B(+), FIG. 11), or in a head to tail (construct A/B(−), FIG. 11) orientation. These constructs were co-transfected into K562 cells in the presence or absence of wt p53, and the activities of both luciferase reporters were measured. The results in FIG. 12C show that genetic unit II within the dual control constructs is strongly stimulated by wt p53 (compare columns 1 and 3 with 2 and 4 respectively, FIG. 12C). In this experiment, no stimulation could be seen of the HSP-70 promoter in genetic unit I, suggesting that the activity of the p53 enhancer sequence in unit II had been successfully isolated by the insulator sequences.

The experimental work will now be described in more detail.

Assays with Ligated vector constructs—dual control units
Materials and methods
Constructs and assay for linked Genetic Units I and II
  Basic constructs:
FIG. 11 A, Hsp70-lacO-tk and Hsp70-lacO-rl
  The human heat-shock gene promoter (−117 to +26) [Tsutsmi-Ishii, 1995] was amplified from the genomic DNA of the human HL-60 cells with pfu polymerase (Stratagen) and cloned at Srf I site of pCR-script™ SK(+) (Cam) (Stratagen) to create Hsp70 in sk. The 467 bp Hind III fragment from pOP13CAT (Stratagen) where three Lac operator sequences are located at an intron was cloned at Hind III site of Hsp70 in sk to create Hsp70-lacO in sk.

The coding region of the HSV thymidine kinase gene was amplified with pfu polymerase from PTK0 and cloned at pSI expression vector (Promega) to create pSltk. The 1.5 kb II/BamHI fragment containing the tk gene as well as polyA+ additional signal was cloned at SaI I site of Hsp70-lacO in sk to create Hsp70-lacO-tk.

The 1.2 kb Nhe I/Bam HI fragment from pRL-nuII (Promega) containing Renilla luciferase gene as well as poly A+ signal was cloned at the Cla I site of Hsp70-lacO-tk (the tk gene is detected out by Cla I digestion from Hsp70-lacO-tk) to create Hsp70-lacO-rl.

FIG. 11 B, tkGC$_3$p53-luc
  The 180 bp Sac I/BgI II fragment containing HSV tk promoter (−109 to +52) was cloned at the Bam HI site of pCR-script™ SK(+) (Cam) (Stratagen) to create tk-sk. GC$_3$p53 element from the human Rb gene promoter [Shiio, 1993] was cloned at Eco RV site of the tk-sk to create tkGC$_3$p53-sk. The 2.0 kb Hind III/Sal I fragment containing the Firefly luciferase gene and poly A+ signal of pGL3Basic was cloned into tkGC$_3$p53-sk to create tkGC$_3$p53-luc.

FIG. 11 C, In/tkGC$_3$p53-luc/In
  The construct (pJC5-4) [Chung, 1993] containing two insulator element from the chicken β-globin locus as well as the local control region and neo gene was provided by G. Felsenfeld. Deletion of both the local control region and neo gene creates pJC5-4-2. The 2.2 kb Xho I/Sal I fragment of tkGC$_3$p53-luc containing the luciferase gene under the control of both GC$_3$p53tk elements was cloned at the Bam HI site of the pJC5-4-2 to create In/tkGC$_3$p53-luc/In.

FIG. 11 D, Dual Constructs
  See FIG. 11D for the details of constructs consisting of Hsp70-lacO-rl (=A) and In/tkGC$_3$p53-luc/In (=B) or tkGC$_3$p53-luc (=C). The 2 kb BssH II fragment containing the Renilla luciferase gene under the control of Hsp 70 promoter and lac Operator of Hsp70-lacO-rl (=A) was cloned at Sal I site of In/tkGC$_3$p53-luc/In (=C) to create A/B+ (referring the head to head arrangement of the two units) and A/B− (referring the head to tail arrangement of the two units). The 2.2 kb Xho I/Sal I fragment of tkGC$_3$p53-luc (=C) was cloned at Bst XI site of Hsp70-lacO-rl (=A) to create A/C+ (referring to the head to tail arrangement of the two units) and A/C− (referring to the head to tail arrangement of the two units).

Results
  The differential effects of the wtp53 over the Unit I and Unit II were maintained in the ligated dual control system when the insulator sequence was included, as shown in FIG. 12. The effect of the insulators on the Unit II response to wtp53 is shown in FIG. 13.

In the experiments of which the results are shown in FIG. 12, K562 cells (0.5 to 1.5×10$^6$ cells/0.4 ml) were transfected by electroporation (260 volts, 1050 μC) with the constructs listed in the brief description given above for FIG. 12 and as indicated in FIG. 12A. Both Firefly and Renilla luciferase activities were measured and the ratio of the luciferase activity of the extracts being co-transfected with wtp53 over that with pCI (p53−) was calculated and plotted. FIG. 12B shows the results for Renilla luciferase, its gene being under the control of the Hsp70 promoter, while FIG. 12C shows the results for Firefly luciferase, its gene being under the control of HSVtk promoter and GC3p53 element.

In the experiments for which the results are shown in FIG. 13, K562 cells were transfected by the constructs listed in the brief description of the figure given above in the combinations given in FIG. 13A. Both Firefly and Renilla luciferase activities were measures in the cell extract on the next day. The results shown in FIGS. 13B, 13C and 13D show that insulator sequence has some inhibitory effect on the HSVtk promoter in Genetic Unit II. Since this effect is more potent when the p53 protein is absent than when present, the insulator elements would enlarge the difference of the potency of the Unit II between the situations where the wtp53 is present or absent.

Results on p53 mediated protein stability
  One of the earliest responses to DNA damage in normal cells is the increased expression level of p53 protein. This has been ascribed to a combination of elevated protein stability, possibly due to phosphorylation induced by a DNA damage recognition process [36, 37], or to increased translatability of the p53 mRNA [7]. For whatever reason, the end result is that for a given level of mRNA, p53 protein is produced and stabilised at higher levels in tumour cells than in the corresponding normal cells [8].

In a parallel series of experiments to those described above to exploit p53 transcriptional control, the differential stability of p53 in normal and tumour cells can be used to stabilise the TK protein in a tumour cell environment. Although the exact mechanism by which increased p53 protein levels are obtained is not yet clear, we have prepared a series of constructs designed to test stablisation of fusion proteins comprising the TK protein together with all or various domains of wild-type p53 in the same way as p53 itself in different tumour cell lines.

Several constructs have been prepared and shown to express the appropriate fusion proteins in vitro. These constructs can be transferred into cell lines which exhibit different levels of expression of p53, presumably as a consequence of differing levels of DNA damage signals which they produce [8]. Modified TK gene fusion constructs that show similar differences in levels of expression in the cell lines as wild-type p53, can be used in order to ensure maximal discrimination in overall levels of TK expression between normal and tumour cells.

The cell line MCF-7 has been previously shown to express wt p53 which is inducible by DNA damage, for example by UV irradiation (8). MCF-7 cells were transfected with a fusion construct encoding TK fused to full length wt p53 and stable transfectants were selected with G418. Western blotting using anti-p53 antibodies showed the presence of a fusion protein of the anticipated molecular size in the transfectants (FIG. 14). Moreover, when these cells were subjected to irradiation with UV light, the p53-TK fusion protein was stabilised and expressed at an increased steady-state level in a manner similar to the endogenous p53 protein (FIG. 14).

The indication is that fusion constructs of this type will be stabilised and expressed at higher levels in tumour cells expressing mutant p53 than in the equivalent normal cells, and may be used for tumour-specific cell killing, either in the context of the tumour-specific gene expression constructs employing transcriptional control as discussed, or not. Such constructs may also be used for killing of tumour cells which express elevated levels of wt p53, since the fusion protein may be stabilised in the same way as the endogenous p53 protein. In some tumours, wild-type p53 is expressed but its normal function is disrupted by interaction with other proteins, as discussed, or by being incorrectly localised in the cytoplasm—where it is stabilised. Examples include some tumours in breast cancer (Moll et al. *PNAS USA* 89:7262–7266, 1992) and neuroblastoma (Moll et al. *PNAS USA* 92: 4407–4411, 1995). The evidence that P53 fusion molecules are stabilised in the manner of wtP53 points to their use in targetting expression of a gene product of interest in such tumour cells, i.e. providing discriminatory expression in such tumour cells as opposed to non-tumour cells.

Testing of constructs for activity in vitro and in vivo

The approaches outlined above enable optimal constructs to be arrived at for the realisation of high expression levels in tumour versus normal cells. The efficacy of these TK constructs in killing tumour cells may be tested in a range of human and mouse cell lines which have been characterised with respect to their tumorigenicity and p53 status. These studies can be carried out both on cells in vitro and in nude mouse tumours.

Those constructs which show the highest ability to kill tumour cells in vitro or in vivo, with minimal effects on primary or immortalised normal cells, may be injected into fertilised mouse eggs in order to generate transgenic mice. Adult animals carrying these constructs in the germ line should express very low or no TK mRNA or protein in normal tissues, but elevated levels should be detectable in tumours induced in the transgenic mice by a variety of procedures. The ability of the constructs to be switched on in a tumour cell environment will be tested by inducing skin tumours in these mice by sequential treatment with initiators and promoters of carcinogenesis. The animals will also be crossed with other strains of transgenic mice which develop tumours as a consequence of carrying an activated oncogene in the germline [38] or with animals carrying non-functional p53 or Rb genes and which spontaneously develop a variety of tumour types including lymphomas and sarcomas at high frequency. The animals will be injected with Ganciclovir in an attempt to induce tumour regression. It should be noted that because of the strategy we have adopted, the highest levels of expression and stability of TK protein would be expected in the most highly malignant tumours.

Further considerations

Various genes are known to incorporate elements which confer stability or susceptibility to degradation, either at the RNA or the protein level, and these may be used to enhance stability or degradation in our constructs, according to whichever characteristic is required.

As regards the antitumour gene to be expressed, HSVTK has been particularly mentioned above, as it is known to convert the prodrug Ganciclovir to a cytotoxic counterpart. However, many other possibilities exist, or will be found, which may be utilised in our constructs, including alternative prodrug activating enzymes, or cytokines such as IL-2 or GM-CSF which increases immune recognition of tumours.

A virus-related approach seems particularly interesting in connection with the present invention. Tumour metastases occur in widely different parts of the body, and a treatment based on systemic infection by a viral vector has the potential to reach virtually all parts of the body. Viral vectors which are used for therapeutic purposes are normally replication-incompetent, but we propose the use of replication-competent viral vectors [39], which can infect all cells but are capable of replication only in tumour cells.

We envisage the use of the dual control element to direct expression of genes which control virus replication to tumour cells. For example a viral polymerase gene (retrovirus or adenovirus) could be placed under the control of the dual promoter, or the function of viral promoters driving expression of proteins required for replication could be disrupted in normal cells by insertion of the binding site for a repressor element controlled by wild type p53, as in FIG. 1. Tumour cell killing will be achieved using the lytic properties of the virus (for adenovirus) or by incorporation of an HSV-TK construct (or another construct encoding a pro-drug activation enzyme) and gancyclovir treatment. Discrimination between normal and tumour cells may be enhanced by the induction of wt p53 which takes place in normal cells upon infection with a DNA tumour virus.

It is also known that very low dose radiation can induce wtp53 in normal cells. Therefore such radiation could be used locally or generally to enhance the suppression of the anti-tumour gene (or viral replication) in normal cells.

TABLE 1

Transfection assays — see FIG. 2 and discussion

|   | tkGC3p53-luc | GC3p53tk-luc | pc1 | wtp53 | wtp53 | mt3 | Ratio* | Luc ($\times 10^{-4}$) |
|---|---|---|---|---|---|---|---|---|
| 1 | 1 μg | | 1 μg | | | | 1 | 59 |
| 2 | 1 μg | | | 0.5 μg | | | 5.79 | 342 |
| 3 | 1 μg | | | | 1.5 μg | | 8.98 | 530 |
| 4 | 1 μg | | | | | 1 μg | 0.69 | 40 |
| 5 | | 1 μg | 1 μg | | | | 1 | 1.8 |
| 7 | | 1 μg | | 0.5 μg | | | 50.33 | 94 |
| 8 | | 1 μg | | | 1.5 μg | | 120.6 | 225 |
| 9 | | 1 μg | | | | 1 μg | 0.816 | 1.5 |

TABLE 2

Transfection assays — see FIG. 3 and discussion
GC$_3$p53pt109-aluc(-)poly A+

|   |   |   |   |   | Ratio/vec. |
|---|---|---|---|---|---|
| 1. | Hsp 70-luc | vector | 1 μg/0.52 μl | | 1 |
| 2. | Hsp 70-luc | wt | 0.25 μg/0.4 μl | | 0.57 |
| 3. | Hsp 70-luc | mt143 | 1 μg/0.56 μl | | 1.1 |
| 4. | Hsp 70-luc | vector | 1 μg/0.52 μl | GC$_3$p53pt109-aluc-poly A+ (1 μg) | 1 |
| 5. | Hsp 70-luc | wt | 0.25 μg/0.4 μl | GC$_3$p53pt109-aluc-poly A+ (1 μg) | 0.48 |
| 6. | Hsp 70-luc | mt143 | 1 μg/0.56 μl | GC$_3$p53pt109-aluc-poly A+ (1 μg) | 1.15 |
| 7. | Hsp 70-luc | vector | 1 μg/0.52 μl | GC$_3$p53pt109-aluc(-)poly A+ (1 μg) | 1 |
| 8. | Hsp 70-luc | wt | 0.25 μg/0.4 μl | GC$_3$p53pt109-aluc(-)poly A+ (1 μg) | 0.75 |
| 9. | Hsp 70-luc | mt143 | 1 μg/0.56 μl | GC$_3$p53pt109-aluc(-)poly A+ (1 μg) | 1.05 |
| 10. | Hsp 70-luc | | | pC1-aluc-poly A+ (1 μg) | 0.36 |

TABLE 3

Transfection assays — see FIG. 4 and discussion

|   | Hsp70-tet07-luc | pC1 | pC1-luc-ribo(9) | pC1-luc-ribo*(2) | Ratio |
|---|---|---|---|---|---|
| 1 | 1.2 μl | 0.48 μl | | | 1 |
| 2 | 1.2 μl | | 0.286 μl | | 0.75 |
| 3 | 1.2 μl | | | 0.3 μl | 0.95 |
| 4 | 1.2 μl | 0.96 μl | | | 1 |
| 5 | 1.2 μl | | 0.572 μl | | 0.68 |
| 6 | 1.2 μl | | | 0.6 μl | 1.02 |

TABLE 4

Transfection assays — see FIG. 5 and discussion

|   | Hsp70-lac0-luc | pC1 | p3'SS* | wtp53 | GC$_3$p53tk-lacR | mtp53** | Ratio |
|---|---|---|---|---|---|---|---|
| 1 | 1 μg | 1 μg | | | | | 1 |
| 2 | 1 μg | | 1 μg | | | | 0.623 |
| 3 | 1 μg | | | 0.5 μg | | | 0.43 |
| 4 | 1 μg | | | 0.5 μg | 1 μg | | 0.35 |
| 5 | 1 μg | | | | | 1 μg | 1.1 |
| 6 | 1 μg | | | | 1 μg | 1 μg | 0.98 |

|   | Hsp70-tet07-luc | (CMV-tetR-KRAB) | | (GC$_3$p53tk-tetR-KRAB) | | Ratio |
|---|---|---|---|---|---|---|
| 7 | 1 μg | 1 μg | | | | 1 |
| 8 | 1 μg | 0.28 μl | | | | 0.24 |
| 9 | 1 μg | | 0.5 μl | | | 0.46 |
| 10 | 1 μg | | 0.5 μl | 0.62 μl | | 0.33 |
| 11 | 1 μg | | | | 0.56 μl | 0.95 |
| 12 | 1 μg | | | 0.62 μl | 0.56 μl | 0.99 |

TABLE 5

Transfection assays — see FIG. 6 and discussion

|   | Hsp70-GA14-luc(8) | pC1 | wtp53 | BCDEF | CDEF | Ratio |
|---|---|---|---|---|---|---|
| 1 | 1 μg | 1 μg | | | | 1 |
| 2 | 1 μg | | 1 μg | | | 0.63 |
| 3 | 1 μg | | | 1 μg | | 0.8 |
| 4 | 1 μg | | | | 1 μg | 0.56 |

TABLE 6

Transfection assays — see FIG. 7 and discussion

| A | B | C | D | E | F | G | H | I |
|---|---|---|---|---|---|---|---|---|
| 1 |   | pC1-GUS | GC$_3$p53tk-luc | pCl | wtp53 | luc |   | GUS |   |
| 2 | 1 | 1 μg | 1 μg | 1 μg |   | 19280 | 1 | 2092000 | 1 |
| 3 | 2 | 1 μg | 1 μg |   | 1 μg | 1926600 | 145 | 914960 | 0.44 |

G: Ratio of the luciferase activity of the extract co-transfected with wtp53 construct over that with pCl.

I. Ratio of the GUS activity of the extract co-transfected with wtp53 construct over that with pCl.

REFERENCES

1. Core, M. E. and M. K. Collins, European Journal of Cancer, 1994. 30A(8): p. 1047–1049.
2. Blaese, R. M. et al., European Journal of Cancer, 1994. 30A(8): P. 1190–1193.
3. Pitts, J., Molecular Carcinogenesis, 1994. 11: p. 127–130.
4. Vile, R. and I. R. Hart, Cancer Research, 1993. 53: p. 962–967.
5. Sikora, K., et al., Annals of the New York Academy of Sciences, 1994. 716: p. 115–124.
6. Lane, D., Nature, 1992. 358: p. 15–16.
7. Mosner, et al (1995). EMBO J., 14:4442–4449.
8. Vojtesek, B. and D. P. Lane, 105, 1993: p. 607–612.
9. El-Deiry, W. S. et al., Cell, 1993. 75: p. 817–825.
10. Zastawny, R. L., et al., Oncogene, 1993. 8: p. 1529–1535.
11. Tsutsumi-Ishii, Y., et al., Cell growth and Differentiation, 1995. 6: p. 1–8.
12. Pavletich, N. P., K. A. Chambers, and C. O. Pabo, Genes and Development, 1993. 7: p. 2556–2564.
13. El-Deiry, W., et al., Nature Genetics, 1992. 1: p. 45–49.
14. Bargonetti, J., et al., Genes and Development, 1993. 7: p: 2565–2574.
15. Wang, Y., et al., Genes and Development, 1993. 7: p. 2575–2586.
16. Hunter, T., Cell, 1993(839–841).
17. Waga, S., et al., 1994. Nature 369: p. 574–578.
18. Selvakumaran, M., et al., Oncogene, 1994. 9: p. 1791–1798.
19. Haldar, S., et al., Cancer Research, 1994. 54: p. 2095–2097.
20. Deb, A., et al., Molecular and Cellular Biology, 1992. 66(10): p. 6164–6170.
21. Morris, G. F. and M. B. Matthews, Journal of Biological Chemistry, 1990. 265(27): p. 16116–16125.
22. Chen, X., et al., Genes and Devlopment, 1993. 7: p. 1837–1849.
23. Pietenpol., J. A. and B. Vogelstein, Nature, 1993. 365: p. 17–18.
24. Ragmov, N., et al., Oncogene, 1993. 8: p. 1183–1193.
25. Liu, X., et al., Molecular and Cellular Biology, 1993. 13: p. 3291–3300.
26. Dittmer, D., et al., Nature genetics, 1993. 4: p. 42–45.
27. Chin, k. V. et al., Science, 1992. 225: p. 459–462.
28. Lu, X. and D. P. Lane, Cell. 1993. 75(4): p. 765–778.
29. Marschall, et al. Cellular and Molecular Neurobiology, 1994. 14(5): p. 523–538.
30. Han, K. and J. L. Manley, Genes and Devlopment, 1993. 7: p. 491–503.
31. Ma, J. and M. Ptashne, Cell, 1992. 48: p. 847–853.
32. Dorsett, D., Genetics, 1993. 134(4): p. 1135–44.
33. Vazquez, J. and P. Schedl, EMBO Journal, 1994. 13(24): p. 5984–5993.
34. Bonifer, et al. EMBO J. 1990, 9: p. 2843–2848.
35. Shiio, et al. Oncogene, 1993. 8: p. 2059–2065.
36. Meek, D. W., Seminars in Cancer Biology, 1994, 5(3): p. 203–210.
37. Maxwell, S. A. and J. A. Roth, Critical Reviews in Oncogenesis, 1994. 5(1): p. 23–57.
38. Bailleul, B., et al., Cell, 1990. 62: p. 697–708.
39. Russell, S. J. Eur. J. Cancer 1994, 30A: p. 1165–1171.
40. Kanshani-Sabet, M. and Scanlon, K. J. 1995, Cancer Gene Therapy, 2(3), 213–223;
41. Mercola, D., and Choen, J. S., 1995, Cancer Gene Therapy: 2(1), 47–59.
42. Chung, et al (1993). Cell, 74:505–514.
43. Greenblatt, et al (1994) Cancer Res. 54: 4855–4878
44. Lane and Bedchimol (1990) Genes Dev. 4: 1–8
45. Levine, et al (1991) Nature 351: 453–456
46. Gossler and Zachgo (1994) "Gene and enhancer screens in ES cells." in Gene Targeting—A Practical Approach, ed. Joyner 1995 181–220
47. Nordeen (1988) Biotechniques 6: 454–457
48. Promega, 1995, Cell Tire 96™ non-radioactive cell proliferation assay Technial Bulletin TB112

What is claimed is:

1. A composition comprising a first nucleic acid construct comprising a first gene encoding an antitumor agent whose expression is controlled by a first promoter whose function is suppressed by a wild-type p53 allele in non-tumour cells relative to tumor cells in which wild-type p53 tumor suppressor function is abrogated, and a second nucleic acid construct comprising a second gene whose gene product suppresses expression of said firs gene, wherein the expression of said second gene is controlled by a second promoter comprising the sequence 5'-PuPuPuC(A/T)(A/T)GPyPyPy-3' (SEQ ID NO:1) and whose function is up-regulated by wild type p53 in non-tumor cells relative to tumor cells in which wild-type p53 tumor suppressor function is abrogated, such that said first gene is expressed in tumor cells and suppressed in non-tumor cells.

2. The composition according to claim 1 wherein said second gene of said second nucleic acid construct encodes an antisense RNA transcript complementary to a sequence within mRNA encoded by said first gene of said first nucleic acid construct.

3. The composition according to claim 1 wherein said second gene of said second nucleic acid construct encodes a ribozyme specific for a sequence within mRNA encoded by said first gene of said first nucleic acid construct.

4. The composition according to claim 1 wherein said second gene of said second nucleic acid construct encodes a sequence-specific transcriptional suppressor and said first nucleic acid construct comprises a binding site recognized by said sequence-specific transcriptional suppressor.

5. The composition according to claim 4 wherein said sequence-specific transcriptional suppressor is a lac operator suppressor.

6. The composition according to claim 4 wherein said sequence-specific transcriptional suppressor comprises a tet repressor DNA-binding domain and a transcriptional suppression domain of the *Drosophila* KRAB transcription factor.

7. The composition according to claim 4 wherein said sequence-specific transcriptional suppressor comprises a Gal-4 DNA-binding domain and a transcriptional suppression domain of the *Drosphila* even-skipped transcription factor.

8. The composition according to claim 1 wherein said first nucleic acid construct and said second nucleic acid construct are each on separate nucleic acid vectors.

9. The composition according to claim 1 wherein said first nucleic acid construct and said second nucleic acid construct are on a single nucleic acid vector.

10. The composition according to claim 9 comprising an insulator sequence between said first nucleic acid construct and said second nucleic acid construct.

11. The composition according to claim 10 wherein said nucleic acid vector is a viral vector.

12. The composition according to claim 1 wherein said second nucleic acid construct comprises SEQ ID NO:1 downstream of a TATA Box and downstream of the transcriptional start site of said second promoter of said second nucleic acid construct.

13. The composition according to claim 1 wherein said first promoter is a HSP70 promoter.

14. The composition according to claim 1, wherein said antitumour agent is a pro-drug activating enzyme.

15. The composition according to claim 14, wherein said pro-drug activating enzyme is a thymidine kinase.

16. An isolated cell containing the first nucleic acid construct and the second nucleic acid construct of the composition according to claim 1.

17. The cell according to claim 16 which is a tumor cell.

18. A method of controlling the proliferation of a tumor cell comprising introduction of the first nucleic acid construct and the second nucleic acid construct of the composition according to claim 1 into the cell in vitro.

19. The composition of claim 1, wherein said first promoter is selected from the group consisting of a HSP70 promoter, a Bcl-2 promoter, a PCNA promoter, a MDR1 promoter, a CMV promoter and a p16$^{INK4}$ promoter.

* * * * *

SEQUENCE LISTING

<160> NUMBER OF SEQ ID NOS: 7

<210> SEQ ID NO 1
<211> LENGTH: 11
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)...(3)

```
<223> OTHER INFORMATION: R may be G or A
<220> FEATURE:
<221> NAME/KEY: misc_feature
<222> LOCATION: 5, 6, 7
<223> OTHER INFORMATION: W may be A or T
<220> FEATURE:
<221> NAME/KEY: misc_feature
<222> LOCATION: (9)...(11)
<223> OTHER INFORMATION: Y may be T or C

<400> SEQUENCE: 1
rrrcwwwgyy y                                                                11

<210> SEQ ID NO 2
<211> LENGTH: 24
<212> TYPE: DNA
<213> ORGANISM: Artificial Sequence
<220> FEATURE:
<223> OTHER INFORMATION: Synthetic construct

<400> SEQUENCE: 2
gcccggactt gcctggactt gcct                                                  24

<210> SEQ ID NO 3
<211> LENGTH: 20
<212> TYPE: DNA
<213> ORGANISM: Artificial Sequence
<220> FEATURE:
<223> OTHER INFORMATION: Synthetic construct

<400> SEQUENCE: 3
ggacttgcct ggacttgcct                                                       20

<210> SEQ ID NO 4
<211> LENGTH: 15
<212> TYPE: DNA
<213> ORGANISM: Artificial Sequence
<220> FEATURE:
<223> OTHER INFORMATION: Synthetic construct

<400> SEQUENCE: 4
guguuguucc auucc                                                            15

<210> SEQ ID NO 5
<211> LENGTH: 36
<212> TYPE: DNA
<213> ORGANISM: Artificial Sequence
<220> FEATURE:
<223> OTHER INFORMATION: Synthetic construct

<400> SEQUENCE: 5
ggaatggctg aagagactgu gaagtcgaaa caacac                                     36

<210> SEQ ID NO 6
<211> LENGTH: 40
<212> TYPE: DNA
<213> ORGANISM: Artificial Sequence
<220> FEATURE:
<223> OTHER INFORMATION: Synthetic construct

<400> SEQUENCE: 6
tcgaggaatg gctgaagaga ctgtgaagtc gaaacaacac                                 40

<210> SEQ ID NO 7
<211> LENGTH: 36
<212> TYPE: DNA
<213> ORGANISM: Artificial Sequence
```

```
<220> FEATURE:
<223> OTHER INFORMATION: Synthetic construct

<400> SEQUENCE: 7
gtgttgtttc gacttcactg actccttagc cattcc                                    36
```